(12) United States Patent
Aqad et al.

(10) Patent No.: US 9,128,372 B2
(45) Date of Patent: Sep. 8, 2015

(54) DENDRITIC COMPOUNDS, PHOTORESIST COMPOSITIONS AND METHODS OF MAKING ELECTRONIC DEVICES

(71) Applicant: Rohm and Haas Electronic Materials LLC, Marlborough, MA (US)

(72) Inventors: Emad Aqad, Northborough, MA (US); Cheng-Bai Xu, Southborough, MA (US); Irvinder Kaur, Westborough, MA (US); Mingqi Li, Shrewsbury, MA (US); Jibin Sun, Menlo Park, CA (US); Cecily Andes, Newton, MA (US)

(73) Assignee: Rohm and Haas Electronic Materials LLC

( * ) Notice: Subject to any disclaimer, the term of this patent is extended or adjusted under 35 U.S.C. 154(b) by 0 days.

(21) Appl. No.: 14/145,551

(22) Filed: Dec. 31, 2013

(65) Prior Publication Data
US 2014/0186770 A1 Jul. 3, 2014

Related U.S. Application Data

(60) Provisional application No. 61/748,023, filed on Dec. 31, 2012.

(51) Int. Cl.
*G03F 7/004* (2006.01)
*G03F 7/20* (2006.01)
*C07C 309/00* (2006.01)
*C07C 69/74* (2006.01)
*C07C 303/32* (2006.01)

(52) U.S. Cl.
CPC .............. *G03F 7/004* (2013.01); *C07C 303/32* (2013.01); *G03F 7/20* (2013.01); *C07C 2103/26* (2013.01)

(58) Field of Classification Search
CPC ....... G03F 7/004; G03F 7/20; C07C 2103/26; C07C 303/32

USPC .............. 430/270.1, 913, 914, 394; 560/117; 562/113
See application file for complete search history.

(56) References Cited

U.S. PATENT DOCUMENTS

| | | | |
|---|---|---|---|
| 7,301,047 B2 | 11/2007 | Yoshida et al. | |
| 7,304,175 B2 | 12/2007 | Harada et al. | |
| 7,569,324 B2 | 8/2009 | Kobayashi et al. | |
| 7,833,690 B2 | 11/2010 | Gonsalves et al. | |
| 8,753,796 B2 | 6/2014 | Ichikawa et al. | |
| 2011/0250538 A1 | 10/2011 | Li et al. | |
| 2012/0141939 A1 | 6/2012 | Thackeray et al. | |
| 2012/0264055 A1* | 10/2012 | Ichikawa et al. | 430/280.1 |
| 2012/0315580 A1 | 12/2012 | Masuyama et al. | |
| 2013/0040096 A1* | 2/2013 | Iwato et al. | 428/98 |
| 2013/0052588 A1* | 2/2013 | Yoshida et al. | 430/285.1 |
| 2013/0280657 A1* | 10/2013 | Kasahara et al. | 430/285.1 |
| 2013/0280658 A1* | 10/2013 | Maruyama | 430/285.1 |

FOREIGN PATENT DOCUMENTS

JP 2012097073 A * 5/2012
JP 2013173732 A * 9/2013

OTHER PUBLICATIONS

Machine translation of JP 2012-097073 (no date).*
Taiwanese Search Report for corresponding Taiwan Application No. 102149241, date of completion, Dec. 9, 2014.
Search Report from corresponding Chinese Application No. 201310757482.0, Apr. 24, 2015.

* cited by examiner

*Primary Examiner* — Amanda C Walke

(57) ABSTRACT

Dendritic compounds are provided. The dendritic compounds include an anionic dendron that has a focal point having an anionic group and a linking group, and a photoreactive cation. The dendritic compounds find particular use as photoacid generators. Also provided are photoresist compositions that include such a dendritic compound, as well as methods of forming electronic devices with the photoresist compositions. The dendritic compounds, photoresist compositions and methods find particular applicability in the manufacture of semiconductor devices.

20 Claims, No Drawings

DENDRITIC COMPOUNDS, PHOTORESIST COMPOSITIONS AND METHODS OF MAKING ELECTRONIC DEVICES

This application claims the benefit of priority under 35 U.S.C. §119(e) to U.S. Provisional Application No. 61/748,023, filed Dec. 31, 2012, the entire contents of which application are incorporated herein by reference.

BACKGROUND

Advanced lithographic techniques such as 193 nm immersion lithography have been developed to achieve high quality and smaller feature sizes in microlithography processes, for purposes of forming ever-smaller logic and memory transistors. It is important to achieve both smaller critical dimension (CD) in the imaged photoresist used in the microlithography process, and for the photoresists to provide both low line edge roughness (LER) and line width roughness (LWR), while still retaining good process control tolerances such as high exposure latitude (EL) and a wide depth of focus (DOE).

To meet the challenges for resist materials raised by high resolution lithography, photoacid generators (PAGs) with low, controllable diffusion properties are desirable, particularly ionic PAGs having a photoreactive cation and diffusion limiting anion. The structure of the PAG anion can affect the overall performance of a photoresist by affecting the interaction of the photoacid generator with other photoresist components. These interactions, in turn, affect the diffusion characteristics of the photogenerated acid. PAG structure and size can greatly affect the homogenous distribution of the PAG in the photoresist film. Defects such as T-topping, foot formation and notching can arise if the PAG is not uniformly distributed within the resist film.

Efforts have been made to limit diffusion and the attendant problems associated with diffusive acids. Photoacid generators in which a perfluoroalkysulfonate group is covalently linked to a single sterically bulky, aliphatic or heteroaliphatic group are known. For example, U.S. Pat. Nos. 7,301,047 B2 and 7,304,175 B2 disclose a bulky photoacid generator in which the sulfonate is linked to an adamantyl group. There remains a need for photoresist compositions including PAGs having controlled acid diffusion, improved miscibility with polymers and improved solubility in formulation solvents and organic developers.

STATEMENT OF INVENTION

According to a first aspect of the invention, provided are dendritic compounds. The dendritic compounds comprise: an anionic dendron comprising a focal point comprising an anionic group and a linking group; and a photoreactive cation.

In accordance with a further aspect of the invention, the dendritic compound is of general formula (I):

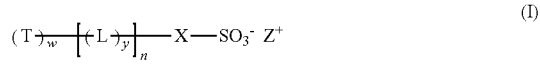

$$(\text{T})_w\text{-}[(\text{L})_y]_n\text{-}X\text{-}SO_3^-\ Z^+ \qquad (I)$$

wherein:
L is a substituted or unsubstituted branched $C_{1-30}$ aliphatic group, $C_{5-30}$ aromatic group or $C_{6-30}$ aralkyl group, having two or more branches with a functional group on each branch, wherein the functional groups are independently chosen from amine, ether, carbonyl, ester, amide, sulfate, sulfonate, sulfonimide, or a combination comprising at least one of the foregoing groups;

X is a substituted or unsubstituted $C_{1-30}$ alkyl, $C_{1-30}$ fluoroalkyl, $C_{3-30}$ cycloalkyl or $C_{3-30}$ fluorocycloalkyl group, optionally comprising an ether, ester, carbonate, amine, amide, urea, sulfate, sulfonate, or sulfonamide containing group;

T is a terminal group comprising a substituted or unsubstituted, $C_5$ or greater cyclic, polycyclic, or fused polycyclic aliphatic group, aromatic group, acid labile group or cyclic lactone, wherein one or more carbon atom in the terminal group can be substituted with a heteroatom;

n is a generation number chosen from integers of 1 or more;

y is the number of linking groups L within a given dendritic generation n and is chosen from integers of 1 or more;

w is the number of terminal branches of linking groups L within the final dendritic generation n and is chosen from integers of 2 or more;

wherein for a first generation (n=1), L is covalently linked to X, and for any subsequent generation (n=2 or greater), L of the subsequent generation is connected to a group L of the previous generation (n−1), and each terminal branch of linking groups L within the final dendritic generation terminates in a terminal group T; and $Z^+$ is a photoreactive cation.

In accordance with a further aspect of the invention, photoresist compositions are provided. The photoresist compositions comprise: an acid-sensitive polymer and a dendritic compound in accordance with the invention.

In accordance with a further aspect of the invention, methods of forming electronic devices are provided. The methods comprise: (a) applying a layer of a photoresist composition in accordance with the invention on a substrate; (b) patternwise exposing the photoresist composition layer to activating radiation; and (c) developing the exposed photoresist composition layer to provide a resist relief image.

All ranges disclosed herein are inclusive of the endpoints, and the endpoints are independently combinable with each other. The suffix "(s)" as used herein is intended to include both the singular and the plural of the term that it modifies, thereby including at least one of that term. "Optional" or "optionally" means that the subsequently described element, event or circumstance can or cannot occur, and that the description includes instances where the event occurs and instances where it does not. As used herein, "combination" is inclusive of blends, mixtures, alloys, or reaction products.

The use of the terms "a" and "an" and "the" and similar referents in the context of describing the invention (especially in the context of the following claims) are to be construed to cover both the singular and the plural, unless otherwise indicated herein or clearly contradicted by context. Further, it should be noted that the terms "first," "second," and the like herein do not denote any order, quantity, or importance, but rather are used to distinguish one element from another.

DETAILED DESCRIPTION

Disclosed herein are novel dendritic compounds having photoreactive cations and sterically bulky anions. The steric bulk of the anions is obtained by the use of an anionic dendron having a focal point comprising an anionic group and a linking group. The dendritic compounds find particular applicability as photoacid generator compounds (PAGs) which, in turn, find particular use in photoresist compositions.

The anionic group of the focal point can include, for example, a fluoroalkylsulfonate group covalently linked to two or more bulky substituent groups through a connecting group (e.g., an alkylene, ether, ester, carbonate, sulfonate, sulfone, sulfonimide, etc.). Suitable bulky substituent groups include, for example, saturated or unsaturated polycyclic hydrocarbons and polycyclic cyclic lactones. A branched chain connects the fluoroalkyl sulfonate group to two or more sterically bulky groups. The counter cation is typically an onium cation, together with the anion forming an onium salt. In this way, a dendritic PAG can be obtained, which can generate a superacid upon exposure to activating radiation.

Chemically amplified photoresists containing such PAGs, imaged with electron beam or at short wavelength radiation (e.g., sub-200 nm radiation including 193 nm and EUV radiation (e.g., 13.5 nm)) are particularly preferred. These dendritic PAGs can exhibit one or more of improved sensitivity, mask fidelity, contrast and resolution as well as good adhesion to substrates. Improved Line Edge Roughness (LWR) can also be obtained. The PAGs typically have solubilities of at least 2 wt % in organic solvents. Such relatively high solubility can be advantagous for both Positive and Negative Tone-Development (PTD and NTD) photoresist processing. Furthermore, the high solubility of the PAGs in organic solvents typically used for photoresist formulation, edge bead removal, etc., improves uniform PAG distribution in the photoresist film, which in turn can provide enhanced photoresist resolution, reduced linewidth roughness (LWR) and improved pattern quality. Such PAG solubility can provide patterned photoresists having low defectivity.

As used herein, "substituted" means including a substituent such as a halogen (i.e., F, Cl, Br, I), hydroxy, amino, thiol, carboxyl, carboxylate, amide, nitrile, thiol, sulfide, disulfide, nitro, a $C_{1-10}$ alkyl, a $C_{1-10}$ alkoxy, a $C_{6-10}$ aryl, a $C_{6-10}$ aryloxy, a $C_{7-10}$ alkyl aryl, a $C_{7-10}$ alkyl aryloxy, or a combination comprising at least one of the foregoing. As used herein, "alkyl aryl" refers to any combination of an alkyl group and aryl group with any order of structural connectivity. Similarly, "alkyl aryloxy" refers to any combination of an alkyl group and aryloxy group with any order of structural connectivity. It will be understood that any group or structure disclosed with respect to the formulas herein may be so substituted unless otherwise specified, or where such substitution would significantly adversely affect the desired properties of the resulting structure. Also as used herein, the prefix "halo-" means that the group includes any halogen or combination thereof (F, Cl, Br, I). A preferred halogen is fluorine.

The prefix "fluoro-" unless otherwise specified includes any group comprising one or more fluorine atom substituents. Also as used herein, the prefix "semifluoro-" means wherein a fluorinated group includes more than one fluorine group, but where fewer than 90% of the available protons are fluorinated. Further, the prefix "perfluoro-" as used herein means wherein greater than 90%, preferably greater than 95%, and more preferably greater than 99% of protons in the parent compound are replaced by fluorine atoms.

Dendrons are monodisperse, wedge-shaped portions of dendrimers, having more than one terminal group branching from a focal point (a single starting moiety) having functional groups. Without limitation, the focal point in the dendrons described herein is preferably derived from a fluoroalkylsulfonate moiety.

Preferred dendritic compounds of the invention include those of the general formula (I):

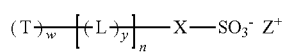

(I)

In Formula (I), L is a substituted or unsubstituted branched $C_{1-30}$ aliphatic group, $C_{5-30}$ aromatic group or $C_{6-30}$ aralkyl group, having two or more branches with a functional group on each branch, wherein the functional groups are independently chosen from amine, ether, carbonyl, ester, amide, sulfate, sulfonate, sulfonimide, or a combination comprising at least one of the foregoing groups. X is a substituted or unsubstituted $C_{1-30}$, preferably $C_{1-10}$, alkyl, $C_{1-30}$, preferably $C_{1-10}$, fluoroalkyl, $C_{3-30}$, preferably $C_{3-10}$, cycloalkyl or $C_{3-30}$, preferably $C_{3-10}$, fluorocycloalkyl group, optionally comprising an ether, ester, carbonate, amine, amide, urea, sulfate, sulfonate, or sulfonamide containing group. T is a terminal group comprising a substituted or unsubstituted, $C_5$ or greater cyclic, polycyclic, or fused polycyclic aliphatic group, aromatic group, acid labile group or cyclic lactone, wherein one or more carbon atom in the terminal group can be substituted with a heteroatom. n is a generation number chosen from integers of 1 or more; y is the number of linking groups L within a given dendritic generation n and is chosen from integers of 1 or more; w is the number of terminal branches of linking groups L within the final dendritic generation n and is chosen from integers of 2 or more. For a first generation (n=1), L is covalently linked to X, and for any subsequent generation (n=2 or greater), L of the subsequent generation is connected to a group L of the previous generation (n−1), and each terminal branch of linking groups L within the final dendritic generation terminates in a terminal group T. $Z^+$ is a photoreactive cation.

Suitable dendritic PAG compounds include, for example, those of the general formula (IIa), (IIb) or (IIc), representing first, second and third generation dendritic PAG structures, respectively:

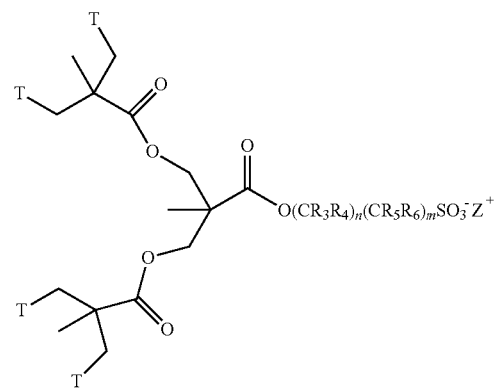

(IIa)

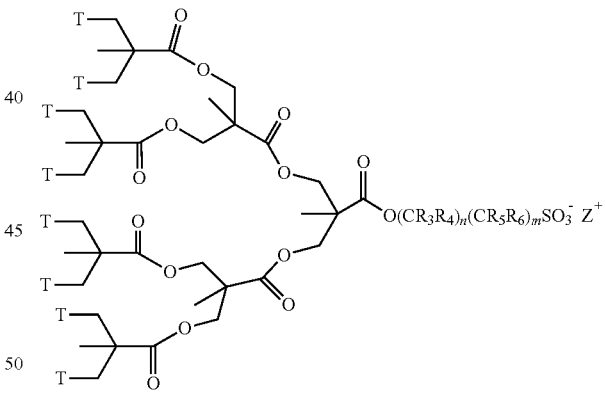

(IIb)

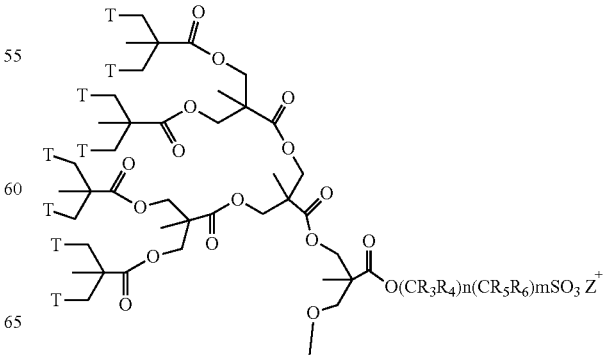

(IIc)

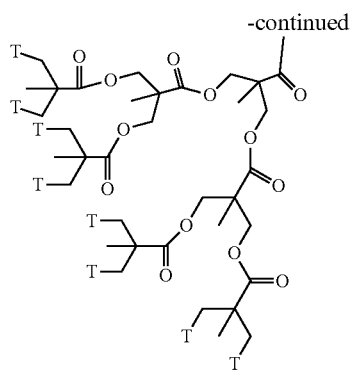
-continued

In the above formulas, each T is independently a $C_5$ or greater cyclic, polycyclic, or fused polycyclic aliphatic group, aromatic group, acid labile group, cyclic lactone, cyclic sultone, a base-labile group, or a base-soluble group, wherein T is optionally substituted with one or more hydroxyl group, cyano group, heteroatom, amine group, ether group or ester group. Each $R_3$ and $R_4$ is independently H, $C_{1-10}$ alkyl, $C_{3-10}$ cycloalkyl or $C_{3-10}$ fluorocycloalkyl. Each $R_5$ and $R_6$ is independently H, F, $C_{1-10}$ alkyl, $C_{1-10}$ fluoroalkyl, $C_{3-10}$ cycloalkyl or $C_{3-10}$ fluorocycloalkyl, wherein at least one of $R_5$ and $R_6$ contains F. $Z^+$ is an organic or inorganic cation, and n and m independently is an integer from 1 to 3.

Preferably, the terminal groups of the dendritic compounds of the invention, represented as "T" in the above-described formulas, include one or more acid labile groups such as tertiary-ester groups, ketal groups and acetal groups. Exemplary dendritic compounds in which the terminal groups are acid cleavable include those of general formulas (IIIa), (IIIb) and (IIIc), representing first, second and third generation dendritic PAG structures, respectively:

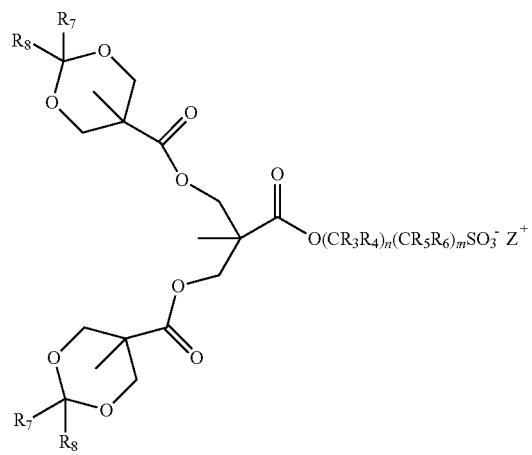
(IIIa)

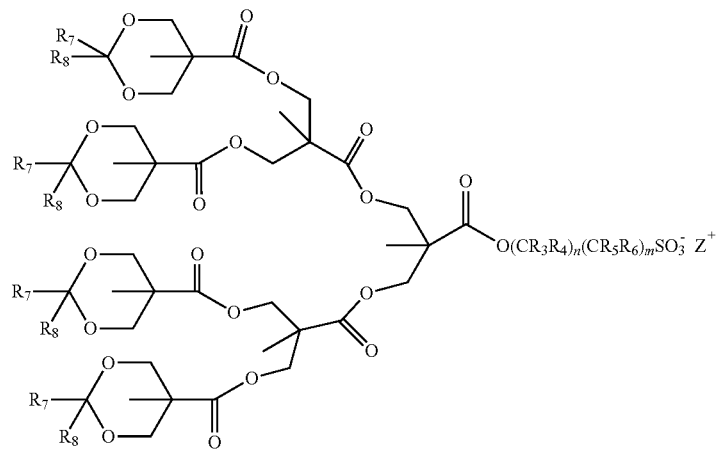
(IIIb)

-continued

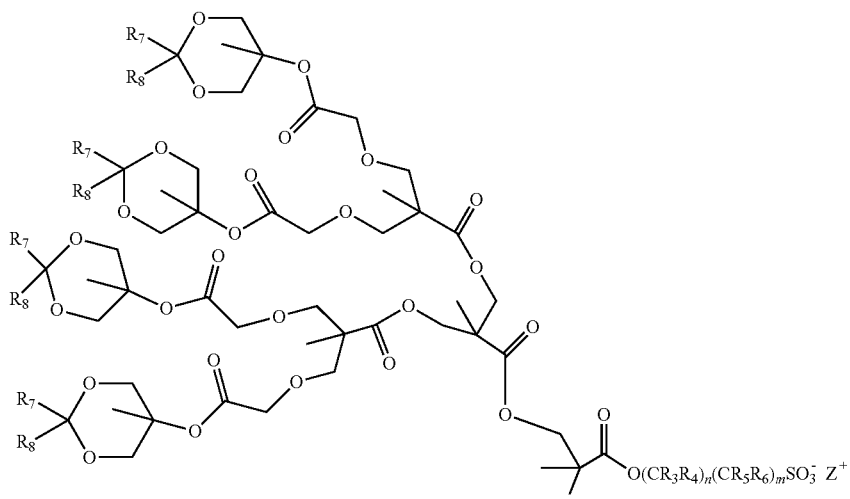

(IIIc)

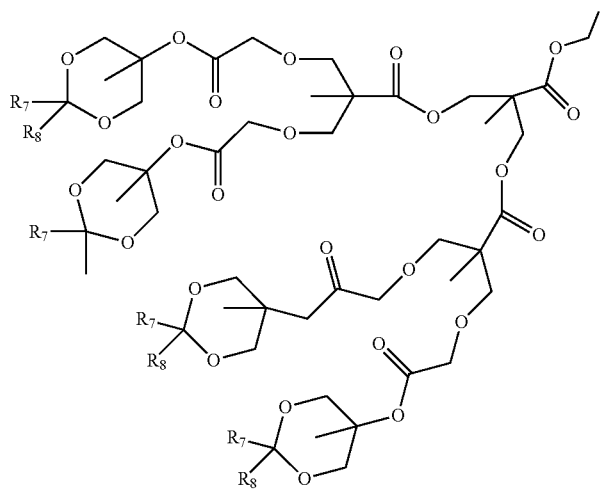

wherein: each R3 and R4 is independently H, $C_{1-10}$ alkyl, $C_{3-10}$ cycloalkyl or $C_{3-10}$ fluorocycloalkyl; each $R_5$ and $R_6$ is independently H, F, $C_{1-10}$ alkyl, $C_{1-10}$ fluoroalkyl, $C_{3-10}$ cycloalkyl or $C_{3-10}$ fluorocycloalkyl; at least one $R^5$ and/or $R^6$ contains F; each $R_7$ and $R_8$ is independently an alkyl, cycloalkyl or substituted cycloalky and together can be connected to form an aliphatic, aromatic or hetertoaromatic cyclic or polycyclic moiety; and $Z^+$ is an organic or inorganic cation.

One or more terminal group may additionally or alternatively to an acid labile group include an unprotected group, for example, a carboxylic acid group, a phenol group or an alkyl alcohol group. Where both types of group are present, the ratio between the number of acid labile groups to unprotected groups on the terminal groups is typically from 1 to 0.2.

The organic or inorganic cation, Z+, is preferably an onium cation, particularly a sulfonium cation. Preferably, $Z^+$ is a cation of the general formula (V):

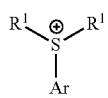

(V)

wherein each $R^1$ is independently a substituted or unsubstituted $C_{1-20}$ alkyl, $C_{1-20}$ fluoroalkyl, $C_{3-20}$ cycloalkyl, $C_{3-20}$ fluorocycloalkyl, $C_{2-20}$ alkenyl, $C_{2-20}$ fluoroalkenyl, $C_{6-20}$ aryl, $C_{6-20}$ fluoroaryl, $C_{5-20}$ heteroaryl, $C_{7-20}$ aralkyl, $C_{7-20}$ fluoroaralkyl, $C_{6-20}$ heteroaralkyl, and Ar is a $C_{5-30}$ aromatic-containing group, wherein the $R^1$ groups together or an $R^1$ group together with the Ar group may form a ring together with the sulfur atom, the ring with the sulfur atom optionally including a heteroatom or a carbonyl group.

Suitable cations for the dendritic compounds include, for example, those of the formulas (VIa), (VIb), (VIc), (VId) or (VIe):

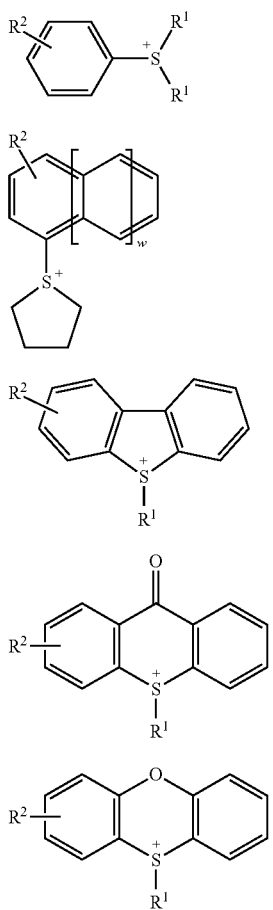

(VIa)

(VIb)

(VIc)

(VId)

(VIe)

wherein each $R^1$ is independently substituted or unsubstituted $C_{1-20}$ alkyl, $C_{1-20}$ fluoroalkyl, $C_{3-20}$ cycloalkyl, $C_{3-20}$ fluorocycloalkyl, $C_{2-20}$ alkenyl, $C_{2-20}$ fluoroalkenyl, $C_{6-20}$ aryl, $C_{6-20}$ fluoroaryl, $C_{5-20}$ heteroaryl, $C_{7-20}$ aralkyl, $C_{7-20}$ fluoroaralkyl, or $C_{6-20}$ heteroaralkyl, wherein $R^1$ is independently unsubstituted or further substituted to include an acid-labile group, a base-labile group, or a base-soluble group, wherein each $R^1$ is separate or is connected to the other $R^1$ and/or to an aromatic group of the cation; and $R^2$ is H, a halogen atom, $C_{1-20}$ alkyl, $C_{1-20}$ fluoroalkyl, $C_{1-20}$ alkoxy, $C_{1-20}$ fluoroalkoxy, $C_{1-20}$ thioalkoxy, $C_{1-20}$ fluorothioalkoxy, $C_{1-20}$ alkoxycarbonyl, $C_{1-20}$ fluoroalkoxycarbonyl, $C_{1-20}$ thioalkoxycarbonyl, $C_{1-20}$ fluorothioalkoxycarbonyl, $C_{3-20}$ cycloalkyl, $C_{3-20}$ fluorocycloalkyl, $C_{3-20}$ cycloalkoxy, $C_{3-20}$ fluorocycloalkoxy, $C_{2-20}$ alkenyl, $C_{2-20}$ fluoroalkenyl, $C_{6-20}$ aryl, $C_{6-20}$ fluoroaryl, $C_{6-20}$ aryloxy, $C_{6-20}$ fluoroaryloxy, $C_{5-20}$ heteroaryl, $C_{5-20}$ heteroaryloxy, $C_{5-20}$ heteroaryloxy, $C_{7-20}$ aralkyl, $C_{7-20}$ fluoroaralkyl, $C_{7-20}$ aralkyloxy $C_{7-20}$ fluoroaralkyloxy, or $C_{6-20}$ heteroaralkyl, or $C_{6-20}$ heteroaralkyloxy, wherein $R^2$ is unsubstituted or substituted to include an acid-labile group, a base-labile group or a base-soluble group, and w is an integer of 1 to 5.

Further exemplary dendritic PAG structures in accordance with the invention include the following:

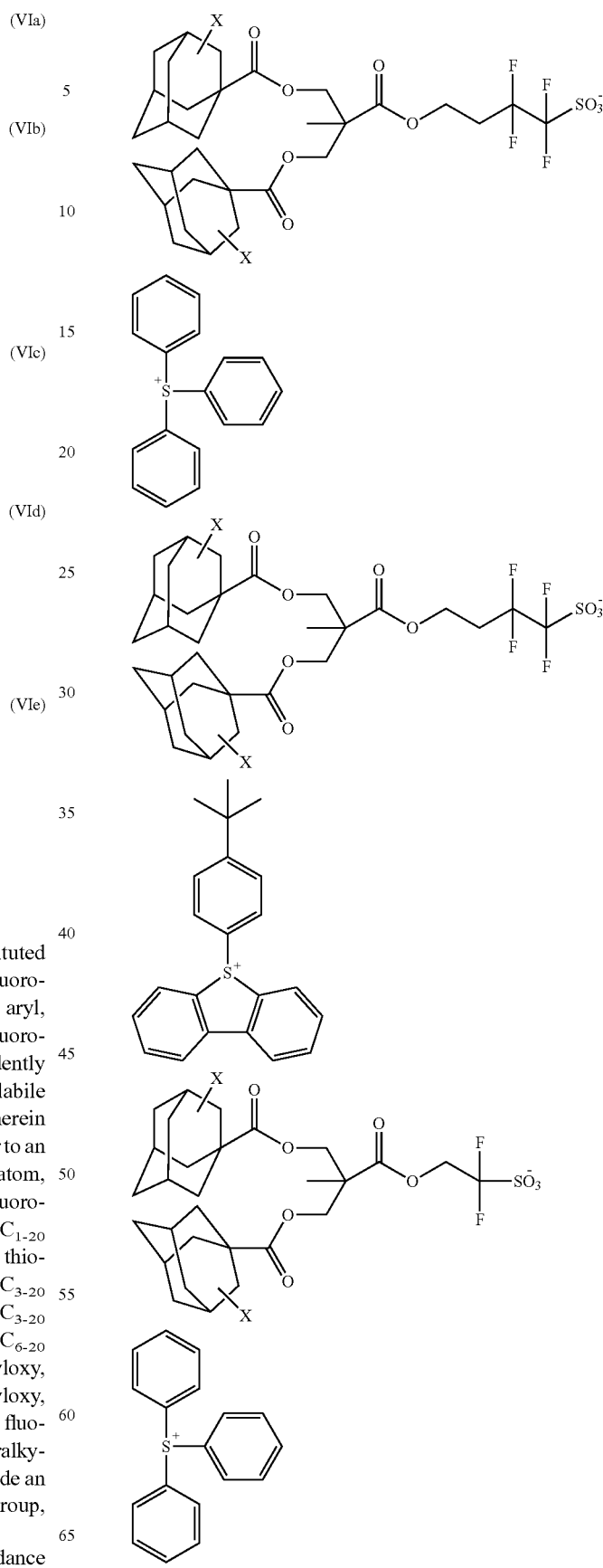

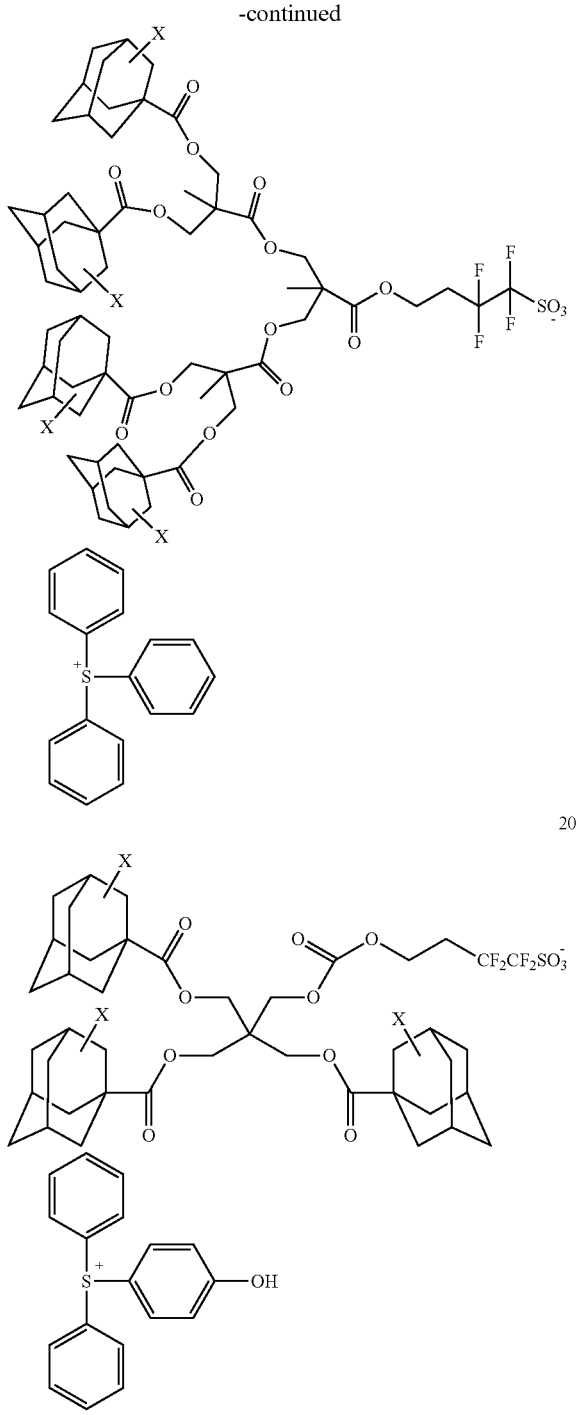

wherein X is H or OH.

The dendritic compounds of the invention can be prepared by known methods. For example, the dendron can be formed by attachment through esterification of a bifunctional or trifunctional aliphatic or aromatic ester-alcohol, with successive addition of a hydroxy-containing cycloaliphatic carboxylic acid compound (e.g., hydroxyadamantane carboxylic acid), followed by optional further reaction of the hydroxy group of the adamantyl with a second bifunctional or trifunctional aliphatic or aromatic ester-alcohol, followed by a second generation of hydroxy-containing cycloaliphatic carboxylic acid compound, until the desired steric bulk or functionality and degree of dendritization is achieved. Methods suitable for forming the anion and cation are well known in the art.

The dendritic compounds find particular use as photoacid generators in a photoresist composition. The dendritic PAGs may be formulated with or combined with a copolymer to form the photoresist. Copolymers useful for forming a photoresist composition in combination with the dendritic photoacid generators disclosed herein include acid deprotectable monomers, base-soluble monomers, dissolution rate modifying monomers, and etch resistant monomers. Any such monomers or combinations of monomers suitable for forming a photoresist polymer useful, for example, at sub 200 nm wavelengths, for example, 193 nm or EUV (e.g., 13.5 nm) wavelengths can be used. Preferably, a combination of monomers is used, which include a (meth)acrylate monomer having an acid deprotectable base soluble group, a (meth)acrylate monomer having a lactone functional group, a (meth)acrylate monomer having a base-soluble group not identical to that of formula (I), or a combination comprising at least one of the foregoing monomers. Other monomers, such as (meth)acrylate monomer for improving adhesion, etch resistance, etc., may also be included.

Any acid-deprotectable monomer useful for forming, for example, a sub-200 nm (e.g., 193 nm or EUV wavelength) photoresist polymer may be used. Exemplary acid-deprotectable monomers include, but are not limited to:

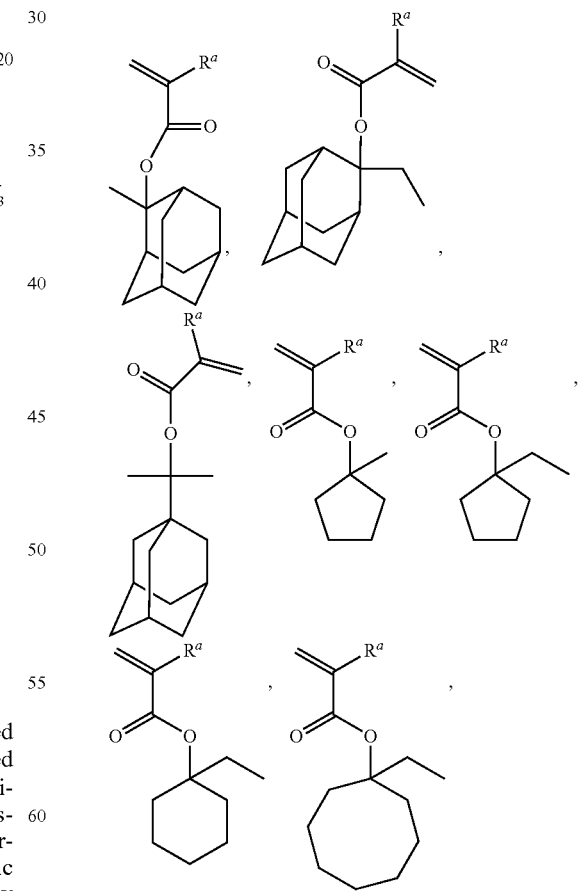

or a combination comprising at least one of the foregoing monomers, wherein $R^a$ is H, F, CN, $C_{1-10}$ alkyl, or $C_{1-10}$ fluoroalkyl.

Any lactone-containing monomer useful for forming a sub-200 nm photoresist polymer may be used. Exemplary such lactone-containing monomers include, but are not limited to:

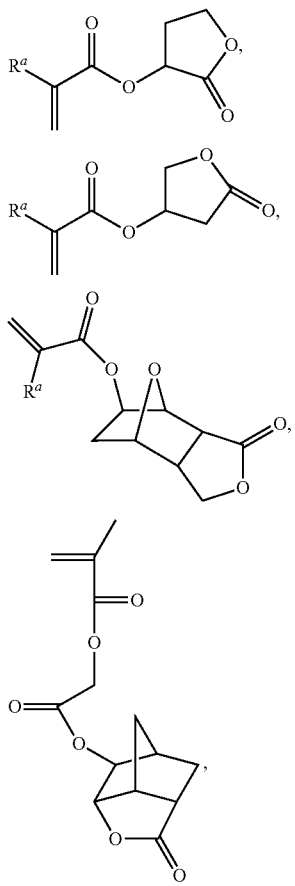

or a combination comprising at least one of the foregoing monomers, wherein $R^a$ is H, F, CN, $C_{1-10}$ alkyl, or $C_{1-10}$ fluoroalkyl.

Any base-soluble monomer useful for forming a photoresist polymer may be used. Exemplary additional base-soluble (meth)acrylate monomers include, but are not limited to:

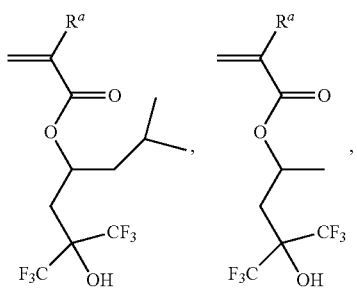

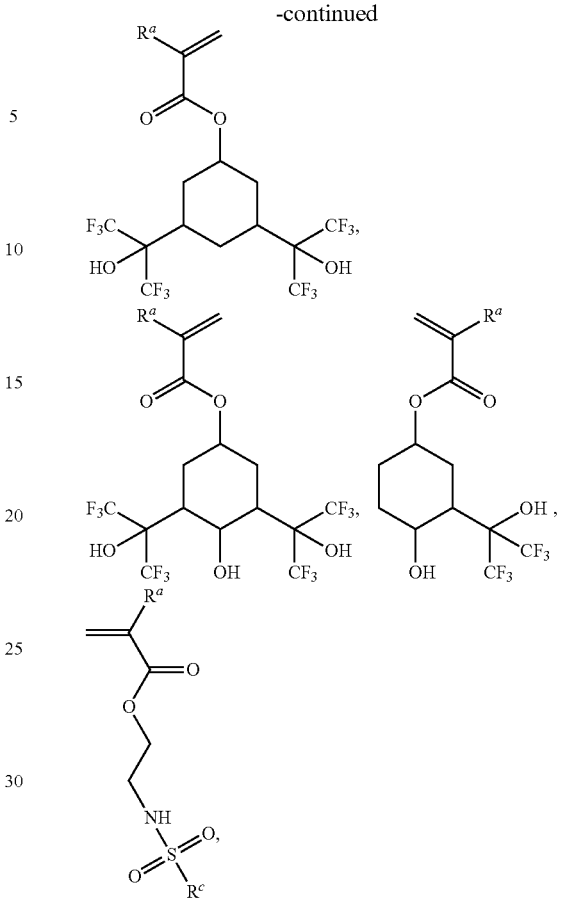

or a combination comprising at least one of the foregoing monomers, wherein $R^a$ is H, F, CN, $C_{1-10}$ alkyl, or $C_{1-10}$ fluoroalkyl, and $R^c$ is a $C_{1-4}$ perfluoroalkyl group.

The polymer may also include other monomers, including cage-structured monomers for enhancing etch resistance, with or without functional groups for improving adhesion. An exemplary adhesion-improving monomer includes:

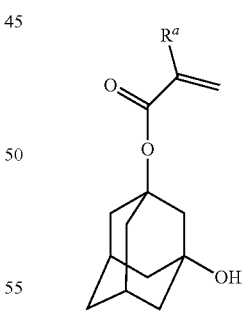

or a combination comprising the foregoing and at least one additional monomer, wherein $R^a$ is H, $C_{1-6}$ alkyl, or $CF_3$.

The photoacid generator is combined with the copolymer, either in admixture or by copolymerization, to form a photoresist. The photoresist optionally further includes a second acid sensitive polymer and/or photoacid generator, an amine or amide additive to adjust photospeed and/or acid diffusion, a solvent, and a surfactant.

The second acid-sensitive polymer may be any polymer suitable for formulating the photoresists for use at sub-200 nm wavelengths. Such acid-sensitive polymers include an acid sensitive polymer comprising acid sensitive groups and lactone-containing groups, where the acid sensitive group deprotects a base-soluble group on exposure to acid.

The photoresist composition may include one or more photoacid generator in addition to the dendritic photoacid generator compound. While the additional photoacid generator may be in additive form (i.e., separate from the matrix polymer), it is preferable that the additional PAG be in polymer-bound form such as where the PAG is bound to the matrix polymer or other polymer in the composition. Suitable additional photoacid generators, additive and polymer bound types are known in the art. Polymer bound photoacid generators are described, for example, in US20120172555A1, US20120171616A1, US20120129105A1 and US20110159429A1. Where an additional polymer bound photoacid generator is used, the polymer bound photoacid generator as the corresponding monomer is typically present in an amount of from 0.01 to 15 wt % based on the total weight of solids.

The photoresist composition may further include an amine or amide compound, referred to herein as a quencher. Quenchers may more broadly include, for example, those based on hydroxides, carboxylates, amines, imines, and amides. A typical quencher is an amine, an amide, or a combination comprising at least one of the foregoing. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as Troger's base, a hindered amine such as diazabicycloundecene (DBU) or diazabicyclononene (DBN), N-protected amines such as N-t-butylcarbonyl-1,1-bis(hydroxymethyl)-2-hydroxyethylamine (TBOC-TRIS), or ionic quenchers including quaternary alkyl ammonium salts such as tetrabutylammonium hydroxide (TBAH) or tetrabutyl ammonium lactate.

Other components of the photoresist may include solvents and surfactants.

Solvents generally suitable for dissolving, dispensing, and coating the components include anisole, alcohols including ethyl lactate, methyl 2-hydroxybutyrate (HBM), 1-methoxy-2-propanol (also referred to as propylene glycol methyl ether, PGME), and 1-ethoxy-2 propanol, esters including n-butylacetate, 1-methoxy-2-propyl acetate (also referred to as propylene glycol methyl ether acetate, PGMEA), methoxyethoxypropionate, ethoxyethoxypropionate, and gamma-butyrolactone, ketones including cyclohexanone and 2-heptanone, and a combination comprising at least one of the foregoing solvents.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The dendrimeric photoacid generator is typically present in the photoresist in an amount of from 0.01 to 20 wt %, preferably from 0.1 to 15 wt %, based on the total weight of solids. The copolymer is typically present in an amount of 50 to 99 wt %, preferably 55 to 95 wt %, more preferably 60 to 90 wt %, and still more preferably 65 to 90 wt % based on the total weight of solids. It will be understood that "polymer" used in this context of a component in a photoresist may mean only the copolymer disclosed herein, or a combination of the polymer with another polymer useful in a photoresist. A surfactant may be included in an amount of 0.01 to 5 wt %, preferably 0.1 to 4 wt %, and still more preferably 0.2 to 3 wt %, based on the total weight of solids. A quencher may be included in relatively small amounts of for example, 0.03 to 5 wt % based on the total weight of solids. Other additives such as embedded barrier layer (EBL) polymer(s) for immersion lithography applications may be included in amounts of less than or equal to 30 wt %, preferably less than or equal to 20%, or more preferably less than or equal to 10%, based on the total weight of solids. The total solids content for the photoresist composition is typically 0.5 to 50 wt %, preferably 1 to 45 wt %, more preferably 2 to 40 wt %, and still more preferably 5 to 35 wt %, based on the total weight of solids and solvent. It will be understood that the solids includes copolymer, photoacid generator, quencher, surfactant, and any optional additives, exclusive of solvent.

The photoresist disclosed herein may be used to form a film comprising the photoresist, where the film on the substrate constitutes a coated substrate. Such a coated substrate includes: (a) a substrate having one or more layers to be patterned on a surface thereof; and (b) a layer of the photoresist composition over the one or more layers to be patterned. Preferably, patterning is carried out using ultraviolet radiation at wavelength of less than 248 nm, and in particular, at 193 nm or EUV (e.g., 13.5 nm) wavelength. The patternable film thus comprises the photoacid generator of formula (I). A method of forming an electronic device therefore includes: (a) applying a layer of a photoresist composition on a substrate; (b) patternwise exposing the photoresist composition layer to actinic radiation; and (c) developing the exposed photoresist composition layer to provide a resist relief image. Preferably, the radiation is 193 nm or EUV (e.g., 13.5 nm) radiation.

Developing the pattern may be accomplished by positive tone development (PTD) in which the patternwise exposed region is removed by the action of an aqueous base developer such as aqueous tetramethylammonium hydroxide (TMAH). An exemplary positive tone developer is 0.26N TMAH (aq.). A method of making a pattern thus includes pattern-wise exposing a photoresist composition layer with actinic radiation, and developing the pattern by treatment with an aqueous alkaline developer to form a positive tone relief image.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 200 mm, 300 mm, or larger in diameter, or other dimensions useful for wafer fabrication production.

The invention is further illustrated by the following non-limiting examples.

EXAMPLES

Example 1

PAG Synthesis of TPS DiAd TFBS

TPS DiAd TFBS (7) was prepared by a five-step synthesis as described in Scheme 1.

Scheme 1

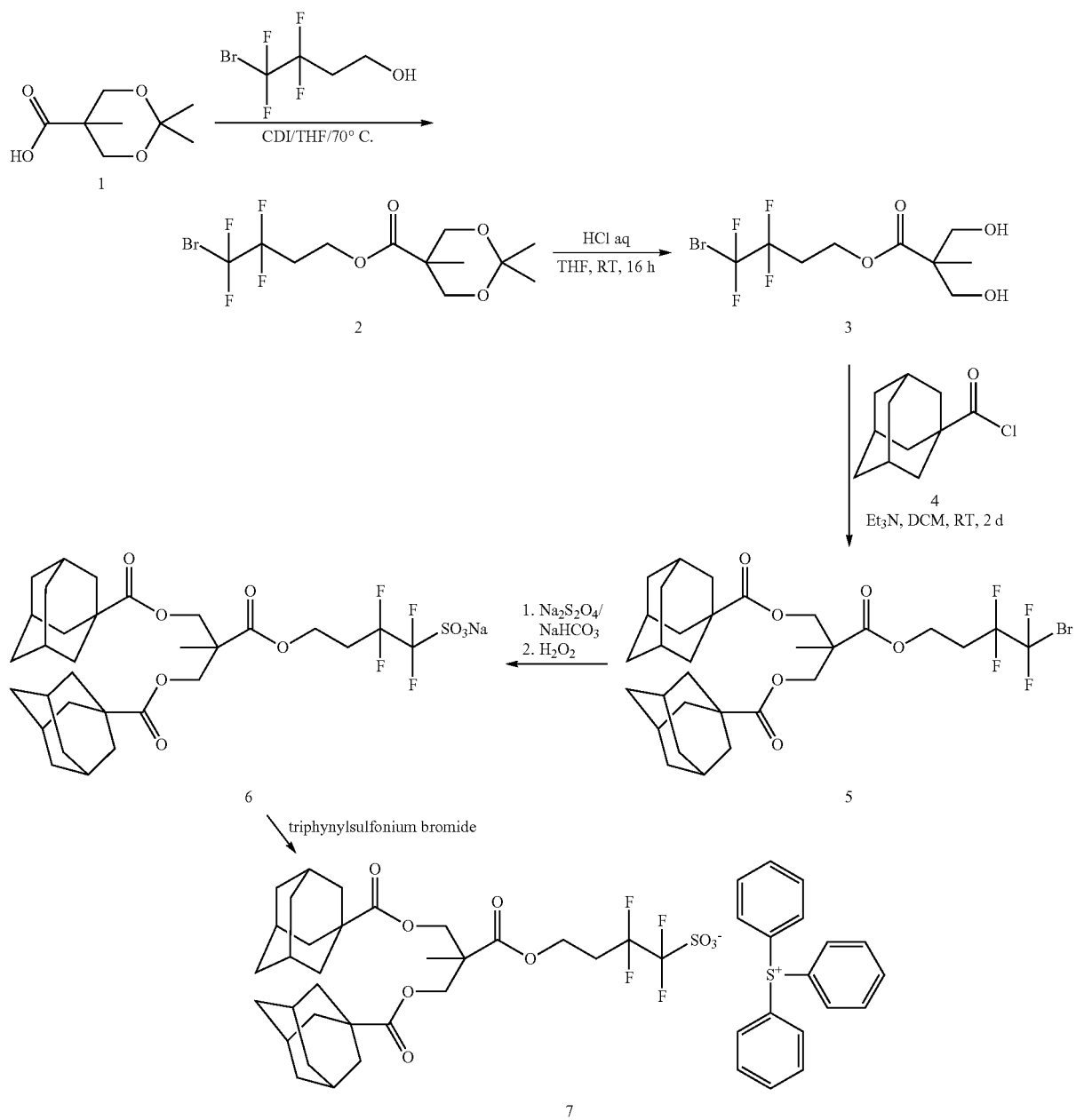

4-Bromo-3,3,4,4-tetrafluorobutyl-2,2,5-trimethyl-1,3-dioxane-5-carboxylate (2) was prepared by the following method. To a solution of isopropylidene-2,2-bis(methoxy) propionic acid (1) (60 g, 344.4 mmol) in 300 mL of anhydrous THF was added 1,1'-carbonyl diimidazole (CDI; 52.8 g, 325.62 mmol) in portions over a 60 min period. After the addition was complete, the reaction was stirred at room temperature for 2 h. The mixture was heated to reflux and 4-bromo-3,3,4,4-tetrafluorobutanol (77.1 g, 344.25 mmol) was added over a 15 min period and the reaction mixture stirred at reflux overnight. The reaction mixture was then cooled to room temperature and the THF removed under reduced pressure. The resulting residue was dissolved in 300 mL of dichloromethane and washed with 0.5N of HCl (3×100 mL) followed by washing with water (5×100 mL). The organic phase was separated, dried over $MgSO_4$ and the solvent was removed under reduced pressure. This produced product 2 as colorless oil which was used in the next step without further purification. Yield 120.0 g (92%). $^1$H NMR (acetone-$d^6$) δ 4.47 (t, 2H), 4.19 (d, 2H), 3.70 (d, 2H), 2.35 (m, 2H), 1.40 (s, 3H), 1.32 (s, 3H), 1.18 (s, 3H). $^{19}$F NMR (acetone-$d^6$) δ −68.07 (s, 2F), −112.17 (s, 2F).

4-Bromo-3,3,4,4-tetrafluorobutyl-3-hydroxy-2-(hydroxymethyl)-2-methylpropanoate (3) was prepared by the following method. To a solution of 4-bromo-3,3,4,4-tetrafluorobutyl 2,2,5-trimethyl-1,3-dioxane-5-carboxylate (2) (100 g, 0.26 mol) in 300 mL THF was added 49 mL of 6N HCl. The reaction mixture was stirred at room temperature (RT) for 16 h, and subsequent work up produced compound (3) as a white solid in 99.5% yield (89 g). $^1$H NMR ($CDCl_3$, 300 MHz): δ 1.06 (s, 3H), 2.51 (m, 2H), 2.79 (bs, 2H), 3.73 (d, 2H), 2.89 (d, 2H), 4.46 (t, 2H). $^{19}$F NMR (CDCl$_3$, 300 MHz): δ −66.82 (s, 2F), −111.38 (s, 2F).

2-((4-bromo-3,3,4,4-tetrafluorobutoxy)carbonyl)-2-methylpropane-1,3-diyl diadamantane carboxylate (5) was prepared by the following method. To an ice cold solution of 4-bromo-3,3,4,4-tetrafluorobutyl 3-hydroxy-2-(hydroxymethyl)-2-methylpropanoate (3) (91 g, 0.27 mol) and adamantyl carbonyl chloride (4, 160 g, 0.81 mol) in 450 mL dichloromethane was added triethylamine (81 g, 0.8 mol) under nitrogen. The reaction mixture was stirred at RT for 36 h. The precipitate was then removed by filtration and the filtrate was washed with 1 N HCl (200 mL), water (2×200 mL), dried on MgSO$_4$, and the solvent removed by rotary evaporation. The resulting residue was purified by silica gel column chromatography to produce pure product (5) in 70% yield (124 g). $^1$H NMR (CDCl$_3$, 300 MHz): δ 1.26 (s, 3H), 1.71 (bs, 12H), 1.85 (bs, 12H), 1.99 (bs, 6H), 2.50 (m, 2H), 4.20 (s, 4H), 4.42 (t, 2H). $^{19}$F NMR (CDCl$_3$, 300 MHz): δ −66.82 (s, 2F), −11.46 (s, 2F).

Sodium 4-(3-(adamantanecarbonyloxy)-2-(adamantanecarbonyloxymethyl)-2-methylpropanoyloxy)-1,1,2,2-tetrafluorobutane-1-sulfonate (6) was prepared by the following method. To a solution of compound (4) (95 g, 0.143 mol) in acetonitrile (350 mL) was added sodium dithionite (50 g, 0.287 mol) and sodium bicarbonate (36 g, 0.428 mol) dissolved in 350 mL deionized water. The reaction mixture was heated to 70° C. and stirred under nitrogen for 16 h. The reaction mixture was cooled to room temperature and the acetonitrile layer was separated. To the acetonitrile solution was added 100 mL of water and hydrogen peroxide, 30% w/w in water (32 g, 2 eq.). The reaction mixture was stirred for 16 h at ambient temperature. The mixture was saturated with NaCl, and the organic phase was separated. The acetonitrile was removed under reduced pressure to produce the crude product 6 in 98% yield (96.32 g). $^{19}$F NMR (acetone-d$_6$, 300 MHz): δ −112.56 (s, 2F), −119.72 (s, 2F).

TPS DiAd TFBS (7) was prepared by the following method. Compound 6 (65 g, 0.094 mol) and triphenylsulfonium bromide (34 g, 0.099 mol) were dissolved in 500 mL dichloromethane and 500 mL deionized water and the reaction mixture was stirred at room temperature for 16 h under nitrogen. The reaction was stopped and the organic layer was separated and washed five times with 200 mL volumes of Millipore deionized water. The dichloromethane from the organic phase was fully removed under reduced pressure to provide the product as a sticky solid. Precipitation of the crude product in methyl t-butyl ether and subsequent drying produce TPS DiAd-TFBS (7): 46% yield (40 g). $^1$H NMR (CDCl$_3$, 300 MHz): δ 1.19 (d, 3H), 1.68 (bs, 12H), 1.84 (bs, 12H), 1.99 (bs, 6H), 2.78 (t, 2H), 4.18 (s, 4H), 4.42 (t, 2H), 7.74 (m, 15H). $^{19}$F NMR (CDCl$_3$, 300 MHz): δ −112.45 (s, 2F), −118.46 (s, 2F).

Example 2

PAG Synthesis of TPS DiAdOH-DFES

TPS DiAdOH-DFES (13) was prepared by a five-step synthesis as described in Scheme 2.

Scheme 2

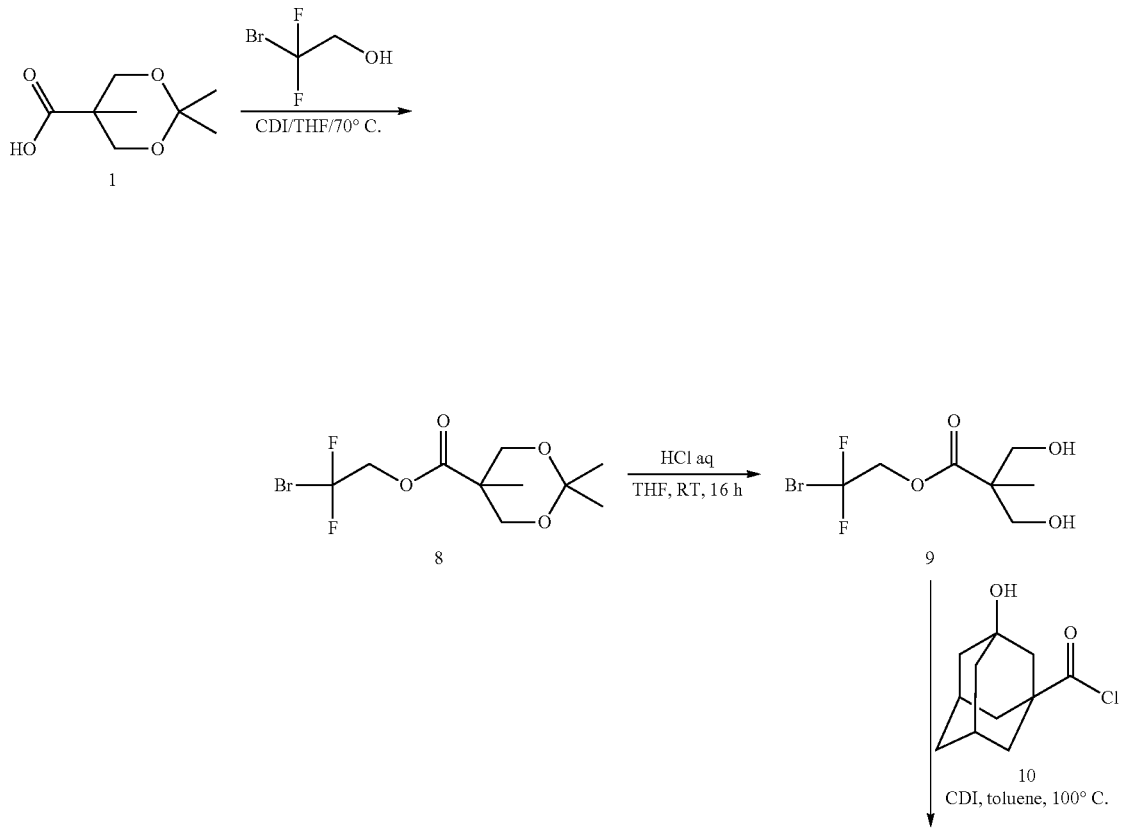

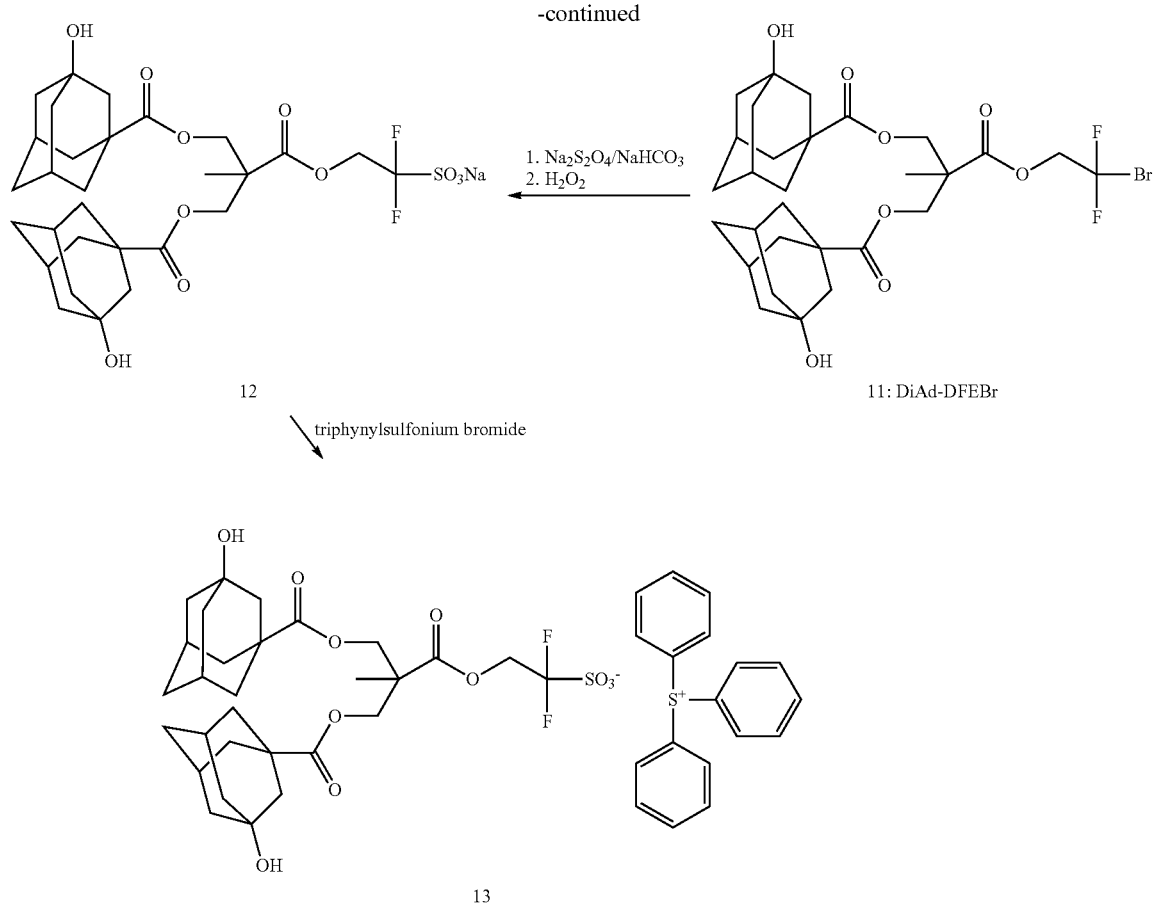

2-Bromo-2,2-difluoroethyl 2,2,5-trimethyl-1,3-dioxane-5-carboxylate (8) was prepared by the following method. To a solution of isopropylidene-2,2-bis(methoxy)propionic acid (1) (50 g, 292.2 mmol) in 300 mL of anhydrous THF was added CDI (44.2 g, 272.58 mmol) in portions over a 60 min period. After the addition was completed the reaction was stirred at room temperature for 2 h. The mixture was heated to reflux and then 2-bromo-2,2-difluoroethanol (46.0 g, 285.8 mmol) was added over a 15 min period. The reaction mixture was stirred at reflux overnight and subsequently cooled to room temperature, and the THF was removed under reduced pressure. The resulting residue was dissolved in 300 mL of dichloromethane and washed with 0.5N of HCl (3×100 mL) followed by washing with water (5×100 mL). The organic phase was separated, dried over $Mg_2SO_4$ and the solvent removed under reduced pressure to produce the product 8 which was used in the next step without further purification. Yield 78.0 g (86%). $^{19}F$ NMR (acetone-$d^6$) δ −57.1 (s, 2F).

2-Bromo-2,2-difluoroethyl 3-hydroxy-2-(hydroxymethyl)-2-methylpropanoate (9): To a solution of product 8 (78 g, 245.0 mmol) in 300 mL THF was added 40 mL of 6N HCl. The reaction mixture was stirred at RT for 16 h. The reaction mixture was poured slowly into solid sodium bicarbonate with gas evolution. NaCl was added and clear THF solution was separated, dried over $MgSO_4$, evaporated to yield compound (3) as white solids in 62% yield (48.8 g).

DiAdOH-DFEBr (11) was prepared by the following method. To a suspension of 3-hydroxyadamantane carboxylic acid (10, 53.6 g, 270.6 mmol) in 300 mL of anhydrous toluene was added CDI (41.0 g, 252.8 mmol) in portions over a 60 min period. After the addition was completed, the reaction was stirred at room temperature for 2 h. The mixture was heated to 100° C. and product 9 (25.0 g, 90.23 mmol) was added. The reaction mixture was stirred at reflux for 2 days. The mixture was cooled to room temperature and the toluene was completely removed under reduced pressure. The resulting residue was dissolved in 300 mL of dichloromethane and washed with 0.5N of HCl (3×100 mL) followed by washing with water (5×100 mL). The organic phase was separated, dried over $MgSO_4$ and the solvent was removed under reduced pressure to produce the product 8 which was used in the next step without further purification. Yield 43.5 g (75%).

DiAdOH-DFES (12) was prepared by the following method. To a solution of compound 11 (60 g, 94.7 mmol) in acetonitrile (350 mL) was added sodium dithionite (36.2 g, 207.9 mmol) and sodium bicarbonate (23.8 g, 283.33 mmol) dissolved in 350 mL deionized water. The reaction mixture was heated to 70° C. and stirred under nitrogen for 16 h. Upon cooling, the phases were allowed to separate. The aqueous layer was then saturated with NaCl(s), and extracted with $CH_3CN$ (100 mL). To the combined organic phase was added deionized water (100 mL). To the rapidly stirred biphasic solution was added 2 equivalents of hydrogen peroxide, 30% w/w in water. The reaction was stirred for 16 h at ambient temperature. The aqueous phase was extracted with two 250 mL volumes of acetonitrile. Evaporation of acetonitrile under reduced pressure produced crude product 12 which was used in the next step without further purification. Yield of crude product 37 g (58%).

TPS DiAdOH-DFES (13) was prepared by the following method. Crude compound 12 (35 g, 0.052 mol) and triphenylsulfonium bromide (16.2 g, 0.047 mol) were dissolved in a mixture of 300 mL dichloromethane and 300 mL deionized water, and the reaction mixture was stirred at room temperature for 16 h under nitrogen, at which time the lower organic layer was separated and washed with deionized water (5×200 mL). The dichloromethane solution was concentrated and poured into large excess of methyl t-butyl ether to precipitate the product, and residual solvent was removed from the product by drying in vacuo to produce the product TPS DiAdOH-DFES (13) in 66% yield (31 g).

Example 3

PAG Synthesis of OHTPS TriAd-TFBS

Synthesis of OHTPS TriAd-TFBS (20) was prepared by the following five-step synthesis as outlined in Scheme 3 and described in the following paragraphs. The detailed synthetic process is presented below.

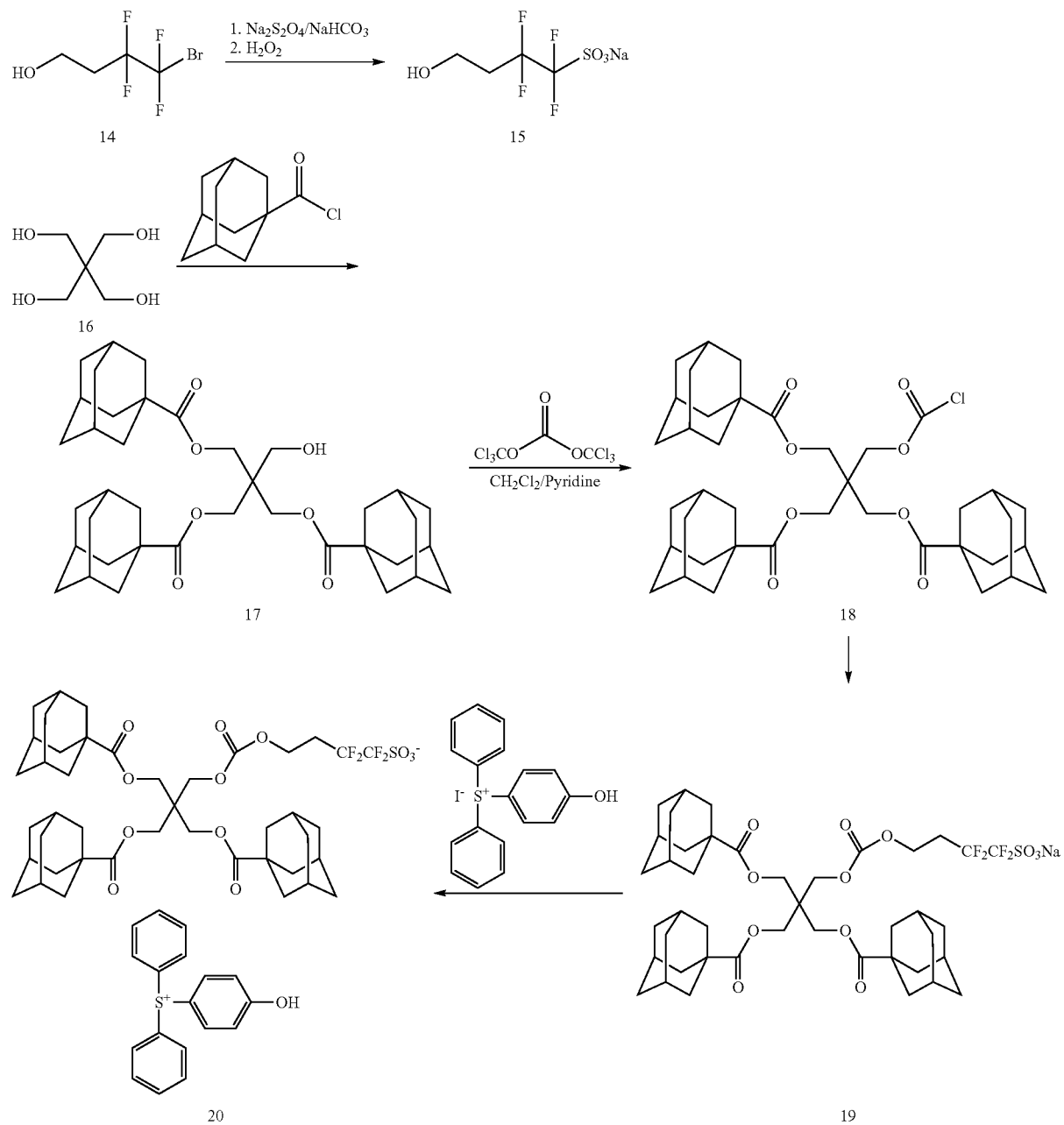

Scheme 3

The synthesis of 1,1,2,2-tetrafluoro-4-hydroxybutane-1-sulfonate sodium salt (15) was achieved as follow: to a solution of 4-bromo-3,3,4,4-tetrafluorobutanol (14, 40.0 g, 177.8 mmol) in 150 mL of acetonitrile was added a solution of sodium dithionite (60 g, 344.6 mmol) and sodium hydrogen carbonate (40 g, 476.2 mmol) in 250 mL of water.

The mixture was stirred at 70° C. for 18 h. The reaction mixture was cooled to room temperature and the solvents were fully removed under reduced pressure. The residue was suspended in 300 mL of acetonitrile and the suspension was heated at reflux with stirring. The undissolved salts were filtered off and to the resulting acetonitrile solution of sodium 1,1,2,2-tetrafluoro-4-hydroxybutane-1-sulfinate was added 50 g of 30% aqueous solution of hydrogen peroxide. The mixture was stirred at room temperature for 18 h. A 50 mL aqueous solution sodium disulfite (5 M) was added to neutralized excess of hydrogen peroxide. The acetonitrile solution was separated and the solvent was removed under reduced pressure to produce 25 g of crude sodium 1,1,2,2-tetrafluoro-4-hydroxybutane-1-sulfonate (15) which was used in the next step without further purification.

To a 2,2-bis(hydroxymethyl)propane-1,3-diol (16, 11.42 g, 0.084 mol) in 500 mL CH$_2$Cl$_2$ solution was added Et$_3$N (25.0 g, 0.25 mol) slowly. This solution was slowly warmed up to 40° C., adamantane-1-carbonyl chloride (50.0 g, 0.25 mol) in 200 mL CH$_2$Cl$_2$ was added drop by drop. The reaction mixture was stirred for 3 days at 40° C. The solution was washed with high purity water (5×150 mL). The organic phase was separated and solvent was removed under vacuum. The result pale white solid was purified by a silica plug with methylene chloride as the eluent. A pale white solid (38.0 g, 73% yield) of 17 was isolated and used in the next step synthesis without further purification. To a solution of compound 17 (6.23 g, 10.0 mmol) in 100 mL methylene chloride was added 15 mL pyridine (excess) and cooled down to ° C. Bis(trichloromethyl) carbonate (1.0 g, 3.4 mmol) in 25 mL methylene chloride was added drop by drop to this solution. The reaction mixture was stirred overnight. Without separation, sodium 1,1,2,2-tetrafluoro-4-hydroxybutane-1-sulfonate (15, 2.5 g, 10.0 mmol) was added all at once. The reaction mixture was stirred at room temperature for 1 day. Solvent was removed and 200 mL methylene chloride was added. This organic solution was washed with high purity water (5×60 mL). The final organic phase was separated and solvent was removed under vacuum, yielding a pale yellow solid. This solid was further purified by silica gel plug with methylene chloride:acetone (95:5) and followed by methylene chloride:acetone (80:20) solvent mixtures as the eluent. The product 19 was obtained as a pure white solid (3.2 g, 36% total yield of the above two steps).

Compound 19 (3.1 g, 3.5 mmol) and (4-Hydroxyl)Phenyl-diphenyl-Sulfonium iodide (1.40 g, 3.4 mmol) were combined in a solution of CH$_2$Cl$_2$/H$_2$O (1:1) 100 mL. The reaction mixture was stirred vigorously at room temperature for 6 hours. The organic phase was separated and washed with high purity water (5×25 mL) and concentrated to 10 mL. This solution was added slowly to 1 L heptanes with vigorously stirring. A white precipitate was formed immediately. Solid was collected and re-dissolved into another 100 mL CH$_2$Cl$_2$. This solution was concentrated again to about 10 mL and repeated the above precipitation for another two times. A crystalline solid was of TPS Tri-Ad-TFBS (20) obtained 2.90 g (73% yield).

Example 4

PAG Synthesis of TPS tetraAd-TFBS

Synthesis of the second generation dendritic photoacid generator TPS tetraAd-TFBS (24) is prepared by the following multi-step synthesis as outlined in Scheme 4 and described in the following paragraphs. Compound 3 is made according to the same synthesis described for Scheme 1. The synthetic process for the other steps is set forth below.

Scheme 4

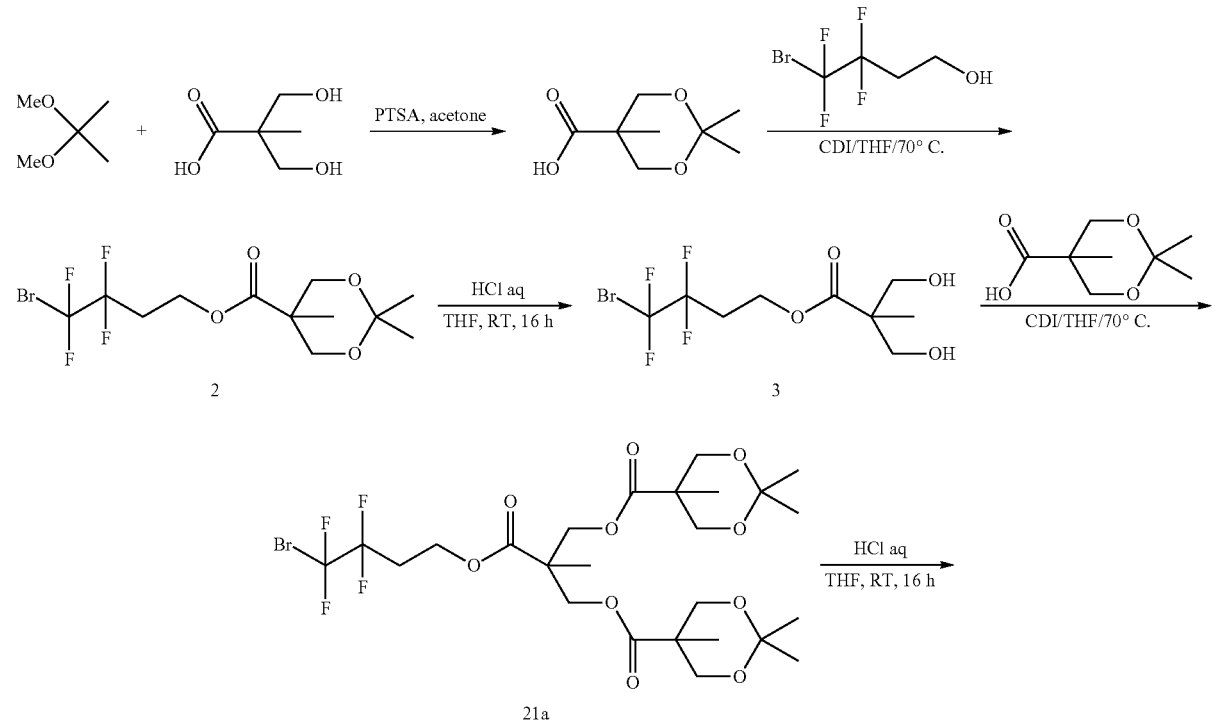

-continued
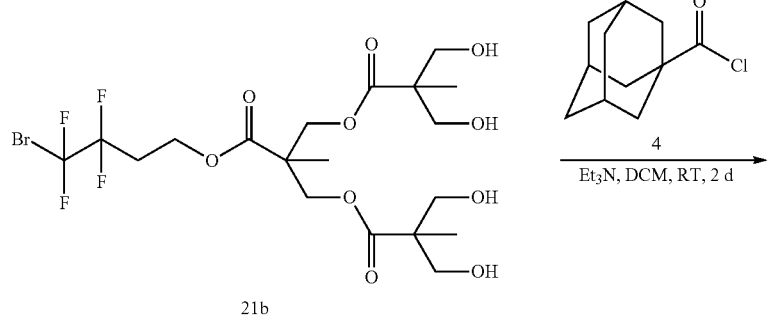
21b
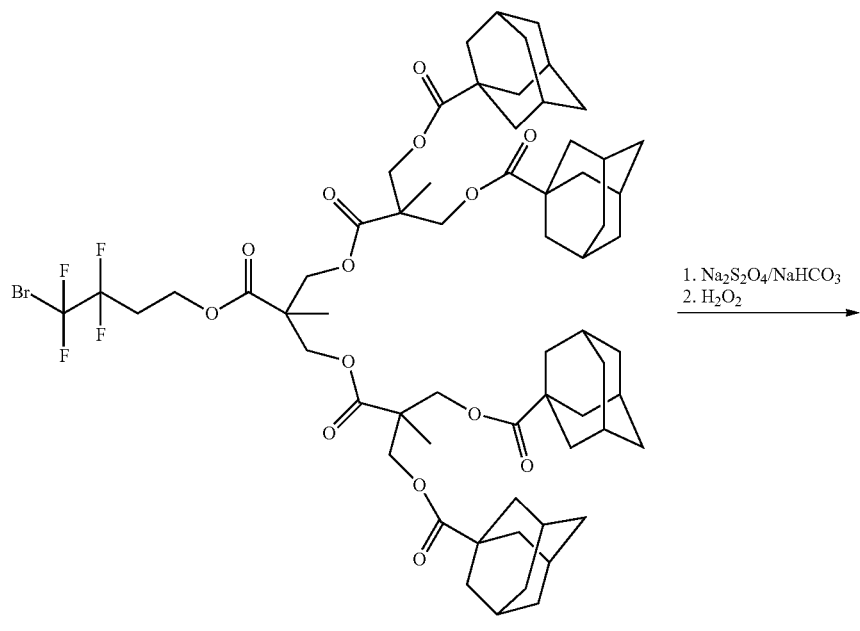
22
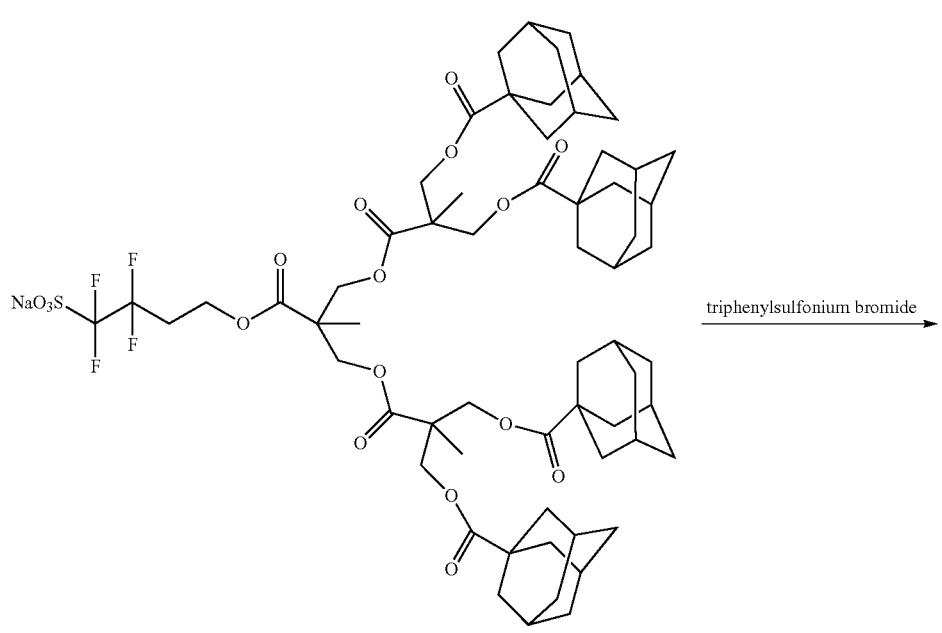
23

-continued

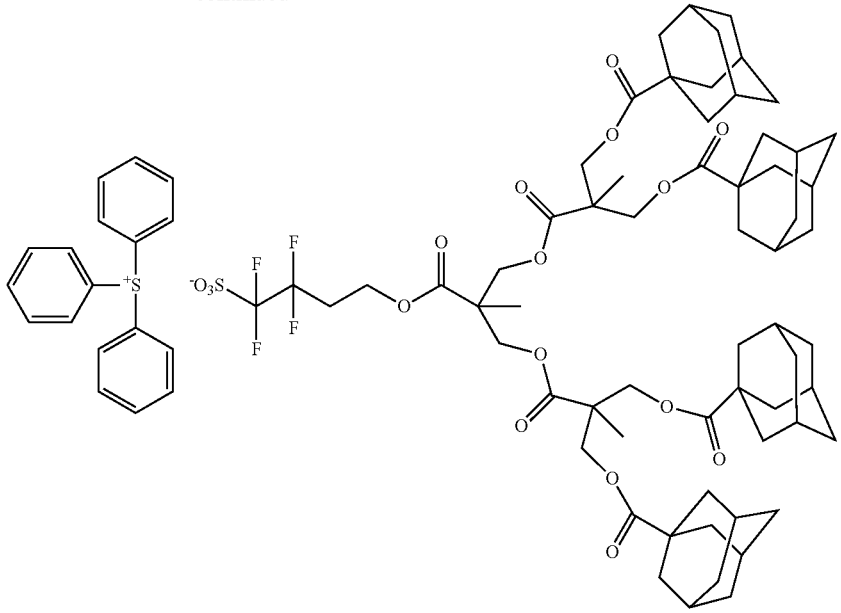

TPS tetraAd-TFBS (24)

To a solution of isopropylidene-2,2-bis(methoxy)propionic acid (60 g, 344.4 mmol in 300 mL of anhydrous THF) is added 1,1'-carbonyl diimidazole (CDI; 52.8 g, 325.62 mmol) in portions. After the addition is complete, the reaction is stirred at room temperature for 2 h. The mixture is heated to reflux and compound 3 (55.7 g, 163.50 mmol) is added over a 15 min period and the reaction mixture is stirred at reflux overnight. The reaction mixture is cooled to room temperature and the THF is removed under reduced pressure. The resulting residue is dissolved in 300 mL of dichloromethane and is washed with 0.5N of HCl (3×100 mL). The organic phase is separated, dried over $Mg_2SO_4$ and the solvent is removed under reduced pressure to produce product 21a, which is used in the next step without further purification. To a solution of compound 21a (100 g, 153.0 mmol) in 600 mL THF is added 100 mL of 6N HCl. The reaction mixture is stirred at RT for 16 h. The reaction mixture is poured slowly into solid sodium bicarbonate. Sodium chloride is added and the clear THF solution is separated, and dried over $MgSO_4$. The THF is fully removed by evaporation under reduced pressure, to leave the pure product 21b. To an ice cold solution of compound 21b (50 g, 87.2 mmol) and adamantyl carbonyl chloride (4, 104.0 g, 523.25 mmol) in 1500 mL dichloromethane is added triethylamine (52 g, 523.25 mol) under nitrogen. The reaction mixture is stirred at RT for 48 h. The precipitate is removed by filtration and the filtrate is washed with 1 N HCl (400 mL), water (2×400 mL). The filtrate is dried on $MgSO_4$, and the solvent is removed by rotary evaporation. The resulting residue is purified by silica gel column chromatography to produce pure product 22. An aqueous solution of sodium dithionite (13.88 g, 79.26 mmol) and sodium bicarbonate (10 g, 119 mmol) in 150 mL water is added to a solution of compound 22 (50 g, 39.8 mmol) in acetonitrile (150 mL) under nitrogen. The reaction mixture is heated to 70° C. for 16 h. The reaction mixture is cooled to room temperature and the upper acetonitrile layer is separated. To the acetonitrile solution is added 100 mL of water and hydrogen peroxide, 30% w/w in water (16 g). The reaction is stirred for 16 h at ambient temperature. The mixture is saturated with NaCl, and the aqueous and organic phases are separated. The acetonitrile is removed under reduced pressure to produce the crude product 23. Precipitating a concentrated acetone solution of 23 in large excess of methyl t-butyl ether produces compound 23 in a pure form. Compound 23 (30 g, 23.48 mmol) and triphenylsulfonium bromide (8.0 g, 23.48 mmol) are dissolved in 100 mL dichloromethane and 100 mL deionized water and the reaction mixture is stirred at room temperature for 16 h. The organic phase is separated and is washed excessively with deionized water. The dichloromethane from the organic phase is fully removed under reduced pressure to provide the crude product TPS tetraAd-TFBS (24). Treatment of crude 24 with mixture of heptanes/methyl t-butyl ether produces pure target material (24).

Acid Diffusion Length Evaluation

Acid diffusion length for various PAGs was determined as follows. An acid detector layer formulation was prepared by combining an acid cleavable polymer (2-adamantyl-2-propyl methacrylate/alpha-(gammabutyrolactone) methacrylate/1-hydroxyadamantyl-3-methacrylate terpolymer, 30/50/20 molar ratio, Mw=10K g/mol) (Polymer A1), shown below (5.981 wt % of total formulation) and tert-butyl 4-hydroxypiperdine-1-carboxylate as a quencher (0.019 wt % of total formulation) in a 50/50 (w/w) mixture of propylene glycol methyl ether acetate (PGMEA) and methyl 2-hydroxyisobutyrate (HBM).

Polymer A1

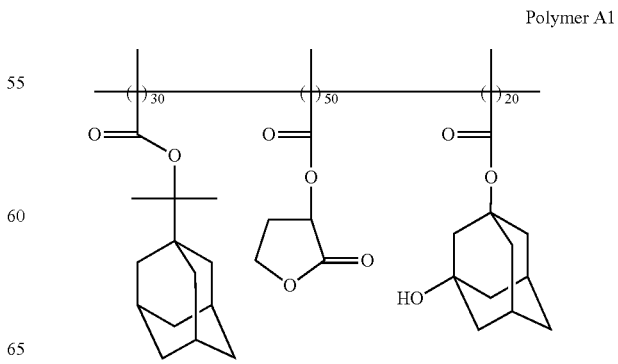

Separately, an acid source layer formulation was prepared by combining a t-butylacrylate/methacrylic acid copolymer (70/30 mol %, respectively, for 100 mol % of monomers; 0.891% w/w solution) and PAG Examples 1 and 2 (153.40 μmol/g based on the total formulation) in an 80/20 (w/w) mixture of 2-methyl-1-butanol and decane. The acid detector layer formulation and acid source layer solutions were each filtered separately using a 0.2 μm polytetrafluoroethylene (PTFE) syringe filter.

The substrate (Si wafer, 200 mm) was coated with AR™77 antireflective coating (Rohm and Haas Electronic Materials, Marlborough, Mass.) and baked at 205° C. for 60 seconds to form an antireflective layer of 84 nm thickness. 120 nm of the acid detector layer formulation was coated on the antireflective layer and baked at 110° C. for 60 seconds. The acid source layer formulation was then coated on the acid detector layer and baked at 90° C. for 60 seconds. All coating processes were carried out on a TEL ACT 8 coating track manufactured by Tokyo Electron.

The coated wafer was then open frame exposed over 100 dose increments (separate doses) starting from an initial dose of 1 mJ/cm² at increments of 0.2 mJ/cm² using a 193 exposure tool (ASML 1100 Stepper) and annular illumination. The wafer was post exposure baked (PEB) at 110° C. for 60 seconds or 120° C. for 60 seconds. During the PEB step the acid released during exposure in the acid source layer diffused into the acid detector layer causing deprotection of the acid labile group of the polymer of the acid detector layer. After PEB, the pattern was developed using 0.26N aqueous tetramethylammonium hydroxide (TMAH) solution. The film thickness difference between the unexposed regions and exposed regions of the pattern is the total film loss (ΔL). The greater the film thickness loss in the exposed region, the greater the acid diffusion.

The diffusivity of the PAG, D, is defined by Fick's law of diffusion (equation 1):

$$D = (\Delta L/2 * erfcE_{th}/E)2/tpEB \qquad \text{(equation 1)}$$

where ΔL is the difference in thickness between the exposed and unexposed areas (also referred to herein as the film thickness loss), $t_{PEB}$ is the PEB time, erfc is the error function complement, $E_{th}$ is the exposure dose (in mJ/cm²) at which film thickness loss was observed for the first time, and E is the exposure dose (in mJ/cm²). Once the diffusivity was determined, the diffusion length, DL, was then calculated using equation 2:

$$DL = 2*(D*tPEB)^{1/2} \qquad \text{(equation 2)}$$

The diffusion length data for PAGs in accordance with the invention and comparative PAGs are summarized below in Table 1.

TABLE 1

| PAG | PAG acid diffusion length (nm) (PEB = 120° C./60 sec) |
|---|---|
| Comp. PAG1 | 55.9 |
| Comp. PAG2 | 47.7 |
| Ex. 1 (TPS DiAd-TFBS) | 15.4 |
| Ex. 2 (TPS-DiAdOH-DFES) | 6.0 |

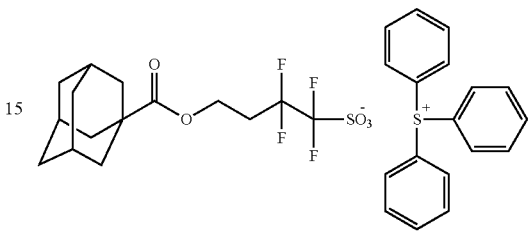

Comparative PAG1

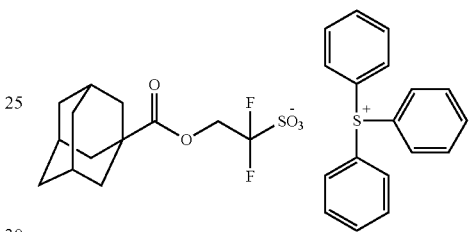

Comparative PAG2

As can be seen in Table 1, the acid diffusion measurements indicate a significantly shorter acid diffusion length for acids that are photogenerated from dendritic PAGs according to the invention in comparison with the comparative PAGs. The low diffusion of dendritic PAGs of the invention is indicative that the dendritic PAGs would allow for the creation of highly resolving photoresists with improved lithographic properties.

PAG Solubility Evaluation

Photoacid generators were evaluated for solubility in various organic solvents finding use in NTD processes and/or as resist formulation solvents. The evaluation was conducted for the PAG of Example 1 (TPS DiAd-TFBS) and Comparative PAG2 using 2 wt % PAG, based on the total weight of the PAG/solvent mixture, at room temperature using various organic solvents. The results are shown in Table 2.

TABLE 2

| Solvent | Solubility Comp. PAG2 | Solubility Ex. 1 (TPS DiAd-TFBS) |
|---|---|---|
| S1 | X | ○ |
| S2 | X | ○ |
| S3 | X | ○ |
| S4 | X | ○ |

S1: Propylene glycol monomethyl ether acetate (PGMEA);
S2: 2-Heptanone;
S3: 1:1 (w/w) blend of 2-heptanone:n-butylpropionate;
S4: n-butylacetate (NBA);
○: compound is completely soluble at 2 wt %;
X: compound is partially soluble or insoluble.

As can be seen from Table 2, the PAG in accordance with the invention of Example 1 (TPS DiAd-TFBS) that comprise two bulky adamantane groups (1$^{St}$ generation dendritic PAG)

exhibited superior solubility characteristics in each solvent tested as compared with Comparative PAG2 which has a single bulky unit.

Examples 5-8

Photoresist Compositions

Photoresists were formulated using the components and proportions shown in Table 3. The formulations contain equimolar PAGs.

wafers were spin-coated with AR™40A antireflectant (Rohm and Haas Electronic Materials) and baked for 60 seconds at 215° C. to yield a first BARC film with a thickness of 840 Å. A second BARC layer was next coated over the first BARC using AR™124 antireflectant (Rohm and Haas Electronic Materials), and was baked at 205° C. for 60 seconds to generate a 200 Å top BARC layer. Photoresist was then coated on the dual BARC-coated wafers and soft-baked at 90° C. for 60 seconds to provide a resist layer with a thickness of 900 Å. The photoresist-coated wafers were exposed through a 6% attenuated phase-shifting mask under single exposure condition. Single exposure processes were carried out through a

TABLE 3

| Resist | Polymer 1 | Polymer 2 | PAG | BASE | Solvent |
|---|---|---|---|---|---|
| Ex. 5 (Comp.) | Polymer A2 (85.324 wt %) | 5 wt % PNBMA/PIBMA 25/75 in PGMEA (2 wt %) | Comp. PAG1 (11.926 wt %) | 1 wt % DDEA in PGMRA (0.75 wt %) | PGMEA/2-HIBAME (35.717 g:38.680 g) |
| Ex. 6 (Comp.) | Polymer A2 (86.498 wt %) | 5 wt % PNBMA/PIBMA 25/75 in PGMEA (2 wt %) | Comp. PAG2 (10.752 wt %) | 1 wt % DDEA in PGMRA (0.75 wt %) | PGMEA/2-HIBAME (35.717 g:38.680 g) |
| Ex. 7 | Polymer A2 (80.222 wt %) | 5 wt % PNBMA/PIBMA 25/75 in PGMEA (2 wt %) | Ex. 1 (TPS DiAD-TFBS) (17.028 wt %) | 1 wt % DDEA in PGMRA (0.75 wt %) | PGMEA/2-HIBAME (35.717 g:38.680 g) |
| Ex. 8 | Polymer A3 | 5 wt % PNBMA/PIBMA 25/75 in PGMEA | Ex. 3 (OHTPS TriAd-TFBS) | tBoc-4HP | 48.5/48.5/3 PGMEA/2-HIBAME/GVL |

PNBMA = Poly(n-butyl methacrylate);
PIBMA = Poly(isobutyl methacrylate);
DDEA = N,N-diethanol dodecanamine;
tBoc-4HP = Butyloxycarbonyl-4-hydroxypyridine;
PGMEA = Propylene glycol methyl ether acetate;
2-HIBAME = 2-hydroxyisobutyric acid methyl ester;
GVL = Gama valerolactone.
All weight percentages (wt %) are based on total solids of photoresist composition.

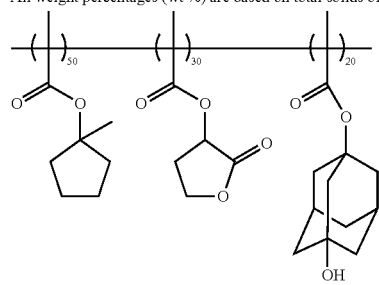

Polymer A2 (MW = 10K)

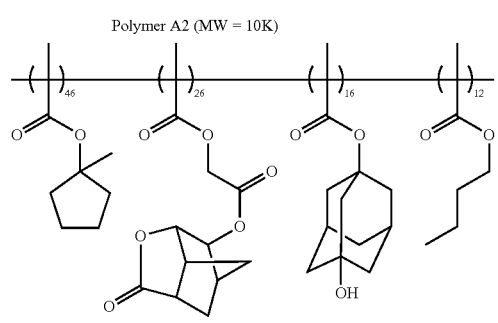

Polymer A3 (MW = 11K)

Lithographic Processing and Evaluation (1)

Immersion lithography was carried out on 300 mm silicon wafers using an ASML Twinscan XT:1900i scanner linked with a TEL Clean Track Lithius i+ coater/developer. Silicon mask having post patterns to print contact hole patterns using an annular illumination with 1.35 NA, 0.97 outer sigma, 0.80 inner sigma and X—Y polarization. The exposed wafers were post-exposure baked at 100° C. for 60 seconds and then developed using n-butyl acetate developer for 25 seconds on a TEL CLEAN TRACK LITHIUS i+ coater/developer to give negative tone patterns. Optimum energy ($E_{op}$) to print 50 nm contact holes was determined by plotting the critical dimension (CD) values, measured on a top-down scanning electron microscope (SEM) (Hitachi CG4000 CD-SEM), as a function of exposure energy using a mask CD at 60 nm (diameter of opaque post on the mask) and a pitch CD at 90 nm (mask CD plus distance between adjacent posts). Critical dimension uniformity (CDU) and Exposure Latitude (EL) were determined by processing the image captured by top-down scanning electron microscopy. CDU was measured as a 3σ of 240 CD values. EL was determined as the difference in exposure energy to print +/−10% of the target diameter normalized by the sizing energy.

TABLE 4

| Resist | PAG | Eop (mJ/cm²) | EL (%) | CDU (3σ, nm) |
|---|---|---|---|---|
| Ex. 5 (Comp.) | Comp. PAG1 | 16.7 | 7.2 | 7.43 |
| Ex. 6 (Comp.) | Comp. PAG2 | 18.7 | 5.6 | 7.85 |
| Ex. 7 | Ex. 1 (TPS DiAd-TFBS) | 32.7 | 7 | 6.81 |

As can be seen from Table 4, the resist formulation of Example 7 in accordance with the invention containing the dendritic PAG compound TPS DiAd-TFBS exhibited a comparable or higher EL as compared with the comparative photoresist examples. In addition, the CDU for the photoresist of Example 7 resulted in a lower (i.e., better) CDU value as compared with the resists of the comparative examples.

Lithographic Processing and Evaluation (2)

Immersion lithography was carried out as described above for Lithographic Processing and Evaluation (1) with the following changes. Single exposure processes were carried out through a mask having contact-hole post patterns (60 nm diameter/112 nm pitch) to print contact hole patterns using a Quad-30 illumination with 1.35 NA, 0.85 outer sigma, 0.65 inner sigma and X—Y polarization. The exposed wafers were post-exposure baked at 100° C. for 60 seconds and then developed in an NTD process using 2-heptanone developer for 25 seconds to give negative tone patterns. The optimum energy ($E_{op}$) to print 53 nm holes, EL and CDU were determined using the procedures described above with respect to Lithographic Processing and Evaluation (1). In addition, Focus Latitude (FL) was determined using the image captured by top-down scanning electron microscopy. Focus latitude (FL) was determined by measuring the length range of focuses over which the critical dimensions remain within +/−10% of the target diameter. The resist pattern profile was visually inspected for fidelity. The results are shown in Table 5.

TABLE 5

| Contact Hole Mask Feature diam/pitch (nm) | Resist | PAG | Eop (mJ) | EL (%) | FL (nm) | CDU (3σ, nm) | Profile |
|---|---|---|---|---|---|---|---|
| 60/112 | Ex. 8 | Ex. 3 (OHTPS TriAd-TFBS) | 40.2 | 9.7 | 180 | 6.75 | ○ |
| 84/800 | Ex. 8 | Ex. 3 (OHTPS TriAd-TFBS) | 40.0 | 11.5 | 100 | 4.21 | ○ |

○: Good photoresist pattern profile based on visual inspection.

What is claimed is:

1. A dendritic compound, comprising:
an anionic dendron comprising a focal point comprising an anionic group and a linking group; and
a photoreactive cation;
wherein the dendritic compound is of general formula (I):

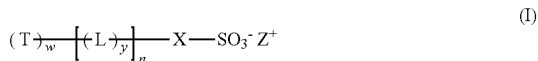

wherein:
L is a substituted or unsubstituted branched $C_{1-30}$ aliphatic group, $C_{5-30}$ aromatic group or $C_{6-30}$ aralkyl group, having two or more branches with a functional group on each branch, wherein the functional groups are independently chosen from amine, ether, carbonyl, ester, amide, sulfate, sulfonate, sulfonimide, or a combination comprising at least one of the foregoing groups;
X is a substituted or unsubstituted $C_{1-30}$ alkyl, $C_{1-30}$ fluoroalkyl, $C_{3-30}$ cycloalkyl or $C_{3-30}$ fluorocycloalkyl group, optionally comprising an ether, ester, carbonate, amine, amide, urea, sulfate, sulfonate, or sulfonamide containing group;
T is a terminal group comprising a substituted or unsubstituted, $C_5$ or greater cyclic, polycyclic, or fused polycyclic aliphatic group, aromatic group, acid labile group or cyclic lactone, wherein one or more carbon atom in the terminal group can be substituted with a heteroatom;
n is a generation number chosen from integers of 2 or more;
y is the number of linking groups L within a given dendritic generation n and is chosen from integers of 1 or more;
w is the number of terminal branches of linking groups L within the final dendritic generation n and is chosen from integers of 2 or more;
wherein for a first generation (n=1), L is covalently linked to X, and for any subsequent generation (n=2 or greater), L of the subsequent generation is connected to a group L of the previous generation (n−1), and each terminal branch of linking groups L within the final dendritic generation terminates in a terminal group T; and
$Z^+$ is a photoreactive cation.

2. The dendritic compound of claim 1, wherein one or more terminal group T comprises an acid labile group.

3. The dendritic compound of claim 1, wherein one or more terminal group T comprises an unprotected group.

4. The dendritic compound of claim 1, wherein $Z^+$ is a cation of general formula (V):

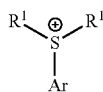
(V)

wherein each $R^1$ is independently a substituted or unsubstituted $C_{1-20}$ alkyl, $C_{1-20}$ fluoroalkyl, $C_{3-20}$ cycloalkyl, $C_{3-20}$ fluorocycloalkyl, $C_{2-20}$ alkenyl, $C_{2-20}$ fluoroalkenyl, $C_{6-20}$ aryl, $C_{6-20}$ fluoroaryl, $C_{5-20}$ heteroaryl, $C_{7-20}$ aralkyl, $C_{7-20}$ fluoroaralkyl, $C_{6-20}$ heteroaralkyl, and Ar is a $C_{5-30}$ aromatic-containing group, wherein the $R^1$ groups together or an $R^1$ group together with the Ar group may form a ring together with the sulfur atom, the ring with the sulfur atom optionally including a heteroatom or a carbonyl group.

5. The dendritic compound of claim 1, wherein Z+ is a cation of the formula VIa, VIb, VIc, VId or VIe:

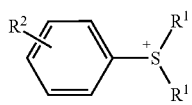
(VIa)

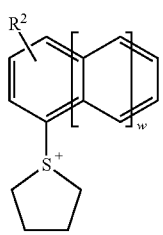
(VIb)

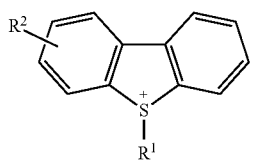
(VIc)

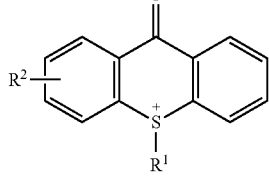
(VId)

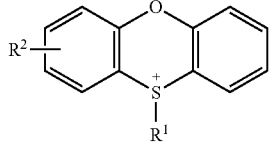
(VIe)

wherein:
each $R^1$ is independently substituted or unsubstituted $C_{1-20}$ alkyl, $C_{1-20}$ fluoroalkyl, $C_{3-20}$ cycloalkyl, $C_{3-20}$ fluorocycloalkyl, $C_{2-20}$ alkenyl, $C_{2-20}$ fluoroalkenyl, $C_{6-20}$ aryl, $C_{6-20}$ fluoroaryl, $C_{5-20}$ heteroaryl, $C_{7-20}$ aralkyl, $C_{7-20}$ fluoroaralkyl, or $C_{6-20}$ heteroaralkyl, wherein $R^1$ is independently unsubstituted or further substituted to include an acid-labile group, a base-labile group, or a base-soluble group, wherein each $R^1$ is separate or is connected to the other $R^1$ and/or to an aromatic group of the cation; and $R^2$ is H, a halogen atom, $C_{1-20}$ alkyl, $C_{1-20}$ fluoroalkyl, $C_{1-20}$ alkoxy, $C_{1-20}$ fluoroalkoxy, $C_{1-20}$ thioalkoxy, $C_{1-20}$ fluorothioalkoxy, $C_{1-20}$ alkoxycarbonyl, $C_{1-20}$ fluoroalkoxycarbonyl, $C_{1-20}$ thioalkoxycarbonyl, $C_{1-20}$ fluorothioalkoxycarbonyl, $C_{3-20}$ cycloalkyl, $C_{3-20}$ fluorocycloalkyl, $C_{3-20}$ cycloalkoxy, $C_{3-20}$ fluorocycloalkoxy, $C_{2-20}$ alkenyl, $C_{2-20}$ fluoroalkenyl, $C_{6-20}$ aryl, $C_{6-20}$ fluoroaryl, $C_{6-20}$ aryloxy, $C_{6-20}$ fluoroaryloxy, $C_{5-20}$ heteroaryl, $C_{5-20}$ heteroaryloxy, $C_{5-20}$ heteroaryloxy, $C_{7-20}$ aralkyl, $C_{7-20}$ fluoroaralkyl, $C_{7-20}$ aralkyloxy $C_{7-20}$ fluoroaralkyloxy, or $C_{6-20}$ heteroaralkyl, or $C_{6-20}$ heteroaralkyloxy, wherein $R^2$ is unsubstituted or substituted to include an acid-labile group, a base-labile group or a base-soluble group, and w is an integer of 1 to 5.

6. A photoresist composition, comprising:
an acid-sensitive polymer, and
a dendritic compound of claim 1.

7. A method of forming an electronic device, comprising:
(a) applying a layer of a photoresist composition of claim 6 on a substrate;
(b) patternwise exposing the photoresist composition layer to activating radiation; and
(c) developing the exposed photoresist composition layer to provide a resist relief image.

8. The method of claim 7, wherein the activating radiation is EUV radiation.

9. The method of claim 7, wherein the developing is conducted with an organic solvent developer.

10. The dendritic compound of claim 1, wherein n=2.

11. The dendritic compound of claim 10, wherein the dendritic compound is of the formula (IIb):

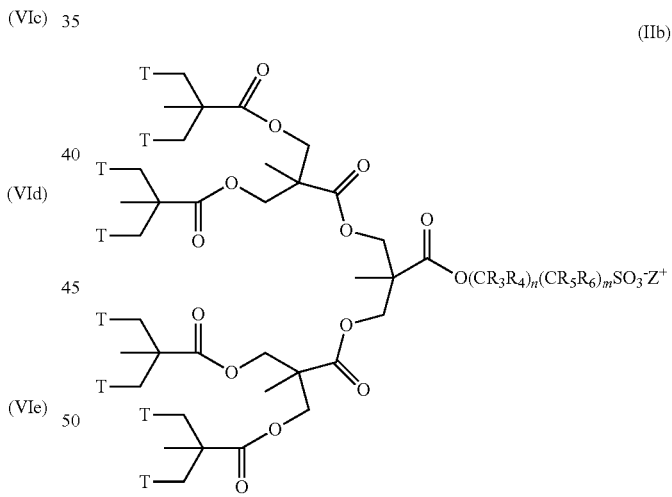
(IIb)

wherein:
each T is independently a $C_5$ or greater cyclic, polycyclic, or fused polycyclic aliphatic group, aromatic group, acid labile group, cyclic lactone, cyclic sultone, base-labile group, or base-soluble group, wherein T is optionally substituted with one or more hydroxyl group, cyano group, heteroatom, amine group, ether group or ester group;
each $R_3$ and $R_4$ is independently H, $C_{1-10}$ alkyl, $C_{3-10}$ cycloalkyl or $C_{3-10}$ fluorocycloalkyl;
each $R_5$ and $R_6$ is independently H, F, $C_{1-10}$ alkyl, $C_{1-10}$ fluoroalkyl, $C_{3-10}$ cycloalkyl or $C_{3-10}$ fluorocycloalkyl, wherein at least one of $R_5$ and $R_6$ contains F;

$Z^+$ is a cation; and n and m are each independently an integer from 1 to 3.

12. The dendritic compound of claim 10, wherein the dendritic compound is of the formula (IIIb):

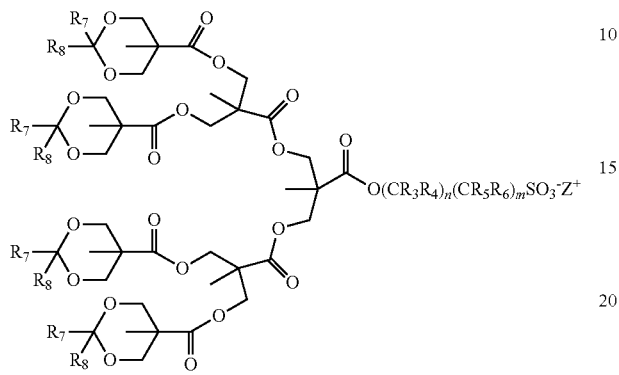

wherein:
- each R3 and R4 is independently H, $C_{1-10}$ alkyl, $C_{3-10}$ cycloalkyl or $C_{3-10}$ fluorocycloalkyl;
- each $R_5$ and $R_6$ is independently H, F, $C_{1-10}$ alkyl, $C_{1-10}$ fluoroalkyl, $C_{3-10}$ cycloalkyl or $C_{3-10}$ fluorocycloalkyl; at least one $R^5$ and/or $R^6$ contains F;
- each $R_7$ and $R_8$ is independently an alkyl, cycloalkyl or substituted cycloalky and together can be connected to form an aliphatic, aromatic or hetertoaromatic cyclic or polycyclic moiety; and
- $Z^+$ is a cation.

13. The dendritic compound of claim 10, wherein the dendritic compound is of the following formula:

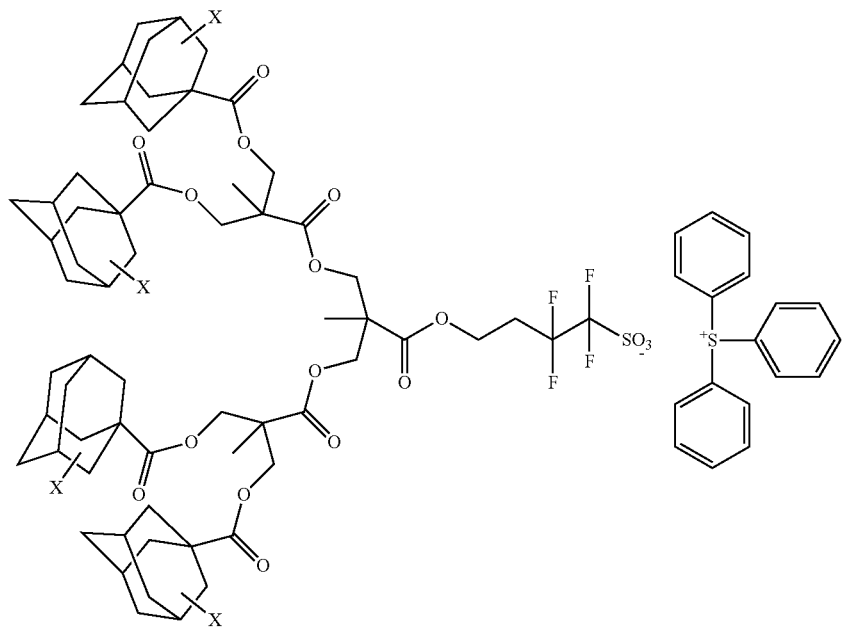

wherein X is H or OH.

14. The dendritic compound of claim 10, wherein the dendritic compound is of the following formula:

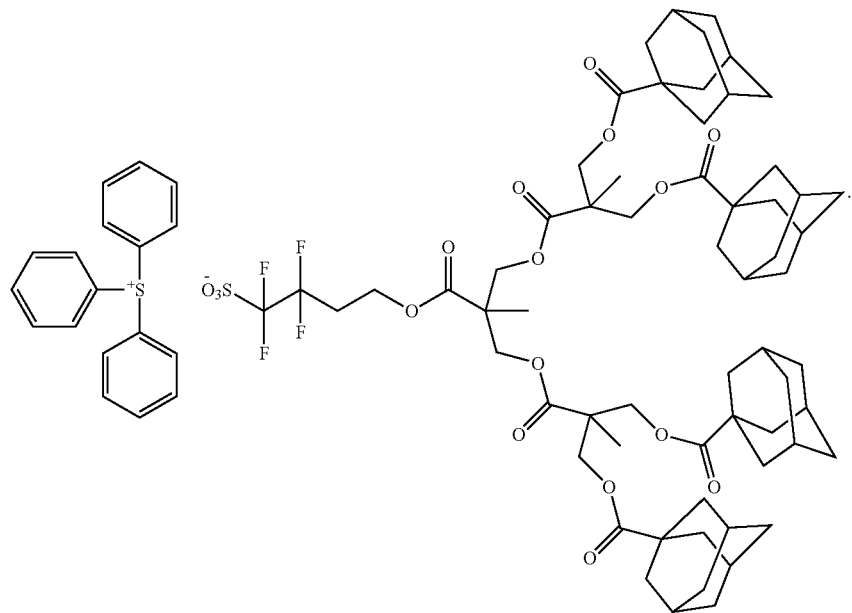
15. The dendritic compound of claim 1, wherein n=3.
16. The dendritic compound of claim 15, wherein the dendritic compound is of the formula (IIc):
(IIc)
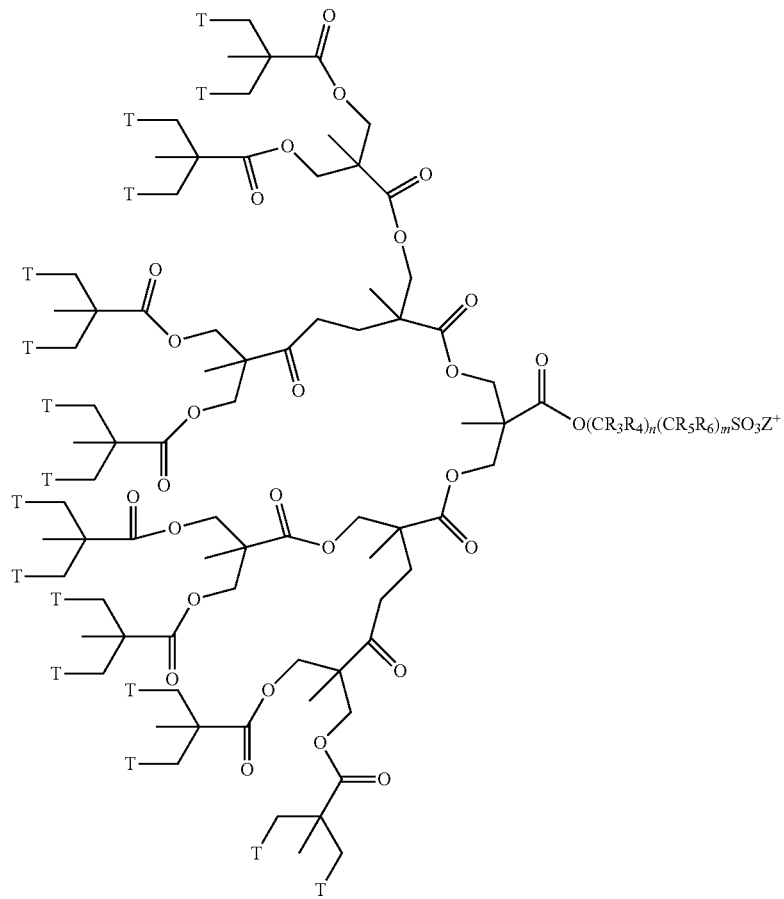
wherein:
each T is independently a $C_5$ or greater cyclic, polycyclic, or fused polycyclic aliphatic group, aromatic group, acid labile group, cyclic lactone, cyclic sultone, base-labile group, or base-soluble group, wherein T is optionally substituted with one or more hydroxyl group, cyano group, heteroatom, amine group, ether group or ester group;

each $R_3$ and $R_4$ is independently H, $C_{1-10}$ alkyl, $C_{3-10}$ cycloalkyl or $C_{3-10}$ fluorocycloalkyl;

each $R_5$ and $R_6$ is independently H, F, $C_{1-10}$ alkyl, $C_{1-10}$ fluoroalkyl, $C_{3-10}$ cycloalkyl or $C_{3-10}$ fluorocycloalkyl, wherein at least one of $R_5$ and $R_6$ contains F;

$Z^+$ is a cation; and n and m are each independently an integer from 1 to 3.

17. The dendritic compound of claim 15, wherein the dendritic compound is of the formula (IIIc):

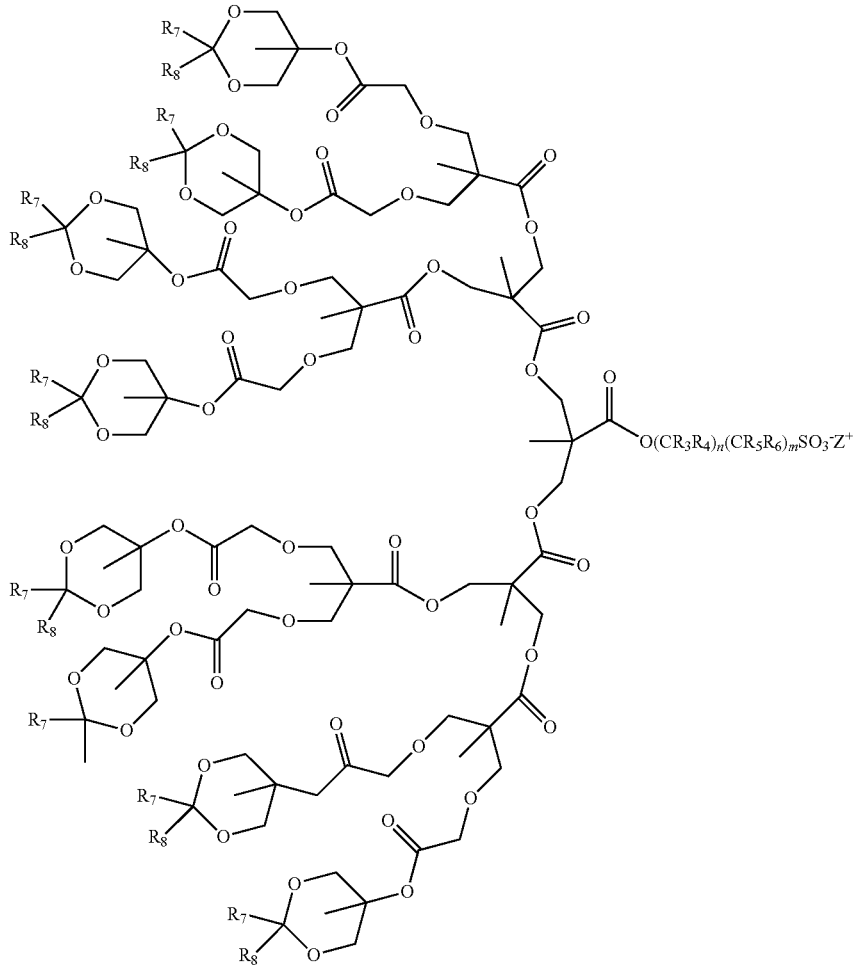

(IIIc)

wherein:
each R3 and R4 is independently H, $C_{1-10}$ alkyl, $C_{3-10}$ cycloalkyl or $C_{3-10}$ fluorocycloalkyl;
each $R_5$ and $R_6$ is independently H, F, $C_{1-10}$ alkyl, $C_{1-10}$ fluoroalkyl, $C_{3-10}$ cycloalkyl or $C_{3-10}$ fluorocycloalkyl; at least one $R^5$ and/or $R^6$ contains F;
each $R_7$ and $R_8$ is independently an alkyl, cycloalkyl or substituted cycloalky and together can be connected to form an aliphatic, aromatic or hetertoaromatic cyclic or polycyclic moiety; and
$Z^+$ is a cation.

18. A dendritic compound chosen from the following compounds:

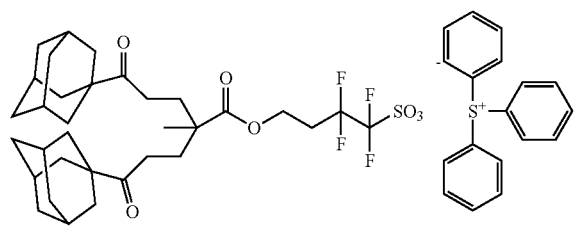
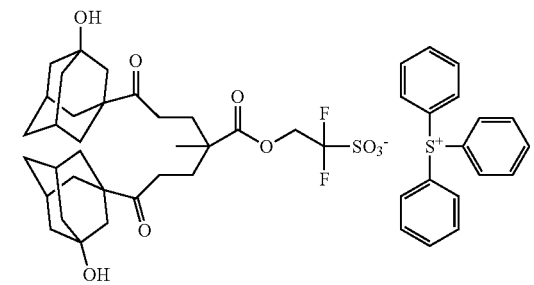
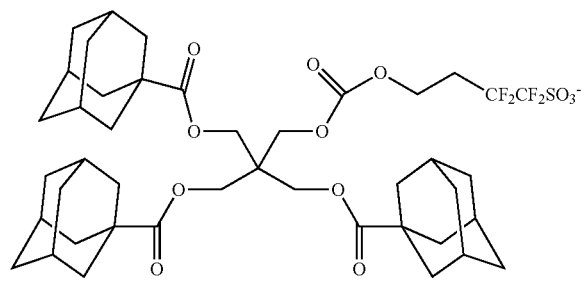
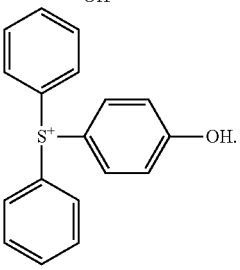

19. A photoresist composition, comprising:
an acid-sensitive polymer, and
a dendritic compound of claim 18.

20. A method of forming an electronic device, comprising:
(a) applying a layer of a photoresist composition of claim 19 on a substrate;

(b) patternwise exposing the photoresist composition layer to activating radiation; and (c) developing the exposed photoresist composition layer to provide a resist relief image.

\* \* \* \* \*